US008039652B2

(12) United States Patent  
Portnoff et al.

(10) Patent No.: US 8,039,652 B2
(45) Date of Patent: Oct. 18, 2011

(54) METHODS FOR PRODUCING BIODIESEL

(75) Inventors: Marc A. Portnoff, Pittsburgh, PA (US); David A. Purta, Gibsonia, PA (US); Margaret A. Nasta, McKeesport, PA (US); Jingfeng Zhang, Gibsonia, PA (US); Faiz Pourarian, Wexford, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 12/760,087

(22) Filed: Apr. 14, 2010

(65) Prior Publication Data

US 2010/0264015 A1 Oct. 21, 2010

Related U.S. Application Data

(63) Continuation of application No. 10/867,627, filed on Jun. 15, 2004, now abandoned.

(51) Int. Cl.
*C11C 3/10* (2006.01)
(52) U.S. Cl. ....................................... 554/169
(58) Field of Classification Search ................ None
See application file for complete search history.

(56) References Cited

U.S. PATENT DOCUMENTS

| 2,383,579 A | 8/1945 | Allen et al. |
| 3,865,855 A | 2/1975 | Linn et al. |
| 3,932,306 A | 1/1976 | Rona |
| 4,102,938 A | 7/1978 | Rao |
| 4,234,402 A | 11/1980 | Kirkbride |
| 4,279,722 A | 7/1981 | Kirkbride |
| 4,300,946 A | 11/1981 | Simons |
| 4,302,436 A | 11/1981 | Sirovich et al. |
| 4,371,469 A | 2/1983 | Foglia et al. |
| 4,389,239 A | 6/1983 | Klatt et al. |
| 4,409,411 A | 10/1983 | Pez |
| 4,456,693 A | 6/1984 | Welsh |
| 4,545,879 A | 10/1985 | Wan et al. |
| 4,555,395 A | 11/1985 | Sirovich et al. |
| 4,560,816 A | 12/1985 | Davis, Jr. |
| 4,604,187 A | 8/1986 | Ward |
| 4,696,806 A | 9/1987 | Peterson et al. |

(Continued)

FOREIGN PATENT DOCUMENTS

DE 19631201 2/1998

(Continued)

OTHER PUBLICATIONS

Noureddini, H., et al., "A Continuous Process for the Conversion of Vegetable Oils into Methyl Esters of Fatty Acids", Journal of the American Oil Chemists' Society, vol. 75, No. 12, pp. 1775-1783, 1998.

(Continued)

*Primary Examiner* — Andrew D Kosar
*Assistant Examiner* — Yate K Cutliff
(74) *Attorney, Agent, or Firm* — Michael Best & Friedrich LLP

(57) ABSTRACT

Transesterification, esterification, and esterification-transesterification (both one-step and two-step) for producing biofuels. The process may be enhanced by one or more of the following: 1) applying microwave or RF energy; 2) passing reactants over a heterogeneous catalyst at sufficiently high velocity to achieve high shear conditions; 3) emulsifying reactants with a homogeneous catalyst; or 4) maintaining the reaction at a pressure at or above autogeneous pressure. Enhanced processes using one or more of these steps can result in higher process rates, higher conversion levels, or both.

22 Claims, 13 Drawing Sheets

U.S. PATENT DOCUMENTS

| | | |
|---|---|---|
| 4,696,873 A | 9/1987 | Yagasaki et al. |
| 4,839,085 A | 6/1989 | Sandrock et al. |
| 4,853,507 A | 8/1989 | Samardzija |
| 4,857,169 A | 8/1989 | Abdo |
| 4,992,605 A | 2/1991 | Craig et al. |
| 5,012,026 A | 4/1991 | Avidan et al. |
| 5,233,109 A | 8/1993 | Chow |
| 5,368,171 A | 11/1994 | Jackson |
| 5,387,397 A | 2/1995 | Strauss et al. |
| 5,455,370 A | 10/1995 | Demmering et al. |
| 5,460,745 A | 10/1995 | Lee |
| 5,508,457 A | 4/1996 | Bayense et al. |
| 5,514,820 A | 5/1996 | Assmann et al. |
| 5,525,126 A | 6/1996 | Basu et al. |
| 5,527,449 A | 6/1996 | Brown et al. |
| 5,532,392 A | 7/1996 | Gheorghiu |
| 5,536,586 A | 7/1996 | Tsushio et al. |
| 5,578,090 A | 11/1996 | Bradin |
| 5,648,483 A | 7/1997 | Granberg et al. |
| 5,705,722 A | 1/1998 | Monnier et al. |
| 5,713,965 A | 2/1998 | Foglia et al. |
| 5,728,271 A | 3/1998 | Piskorz et al. |
| 5,882,623 A | 3/1999 | Zaluska et al. |
| 5,908,946 A | 6/1999 | Stern et al. |
| 5,911,885 A | 6/1999 | Owens |
| 5,914,014 A | 6/1999 | Kartchner |
| 5,972,057 A | 10/1999 | Hayafuji et al. |
| 6,013,387 A | 1/2000 | Yao et al. |
| 6,017,845 A | 1/2000 | Ovalles et al. |
| 6,077,400 A | 6/2000 | Kartchner |
| 6,080,381 A | 6/2000 | Zaluska et al. |
| 6,086,830 A | 7/2000 | Kartchner |
| 6,090,959 A | 7/2000 | Hirano et al. |
| 6,106,675 A | 8/2000 | Tanner et al. |
| 6,147,196 A | 11/2000 | Stern et al. |
| 6,165,643 A | 12/2000 | Doyle et al. |
| 6,171,475 B1 | 1/2001 | Dufaud et al. |
| 6,171,479 B1 | 1/2001 | Ovalles et al. |
| 6,174,501 B1 | 1/2001 | Noureddini |
| 6,175,037 B1 | 1/2001 | Tweedy |
| 6,211,390 B1 | 4/2001 | Peter et al. |
| 6,242,723 B1 | 6/2001 | Lautenschlager |
| 6,262,285 B1 | 7/2001 | McDonald |
| 6,268,596 B1 | 7/2001 | Lauf et al. |
| 6,288,251 B1 | 9/2001 | Tsuto et al. |
| 6,403,939 B1 | 6/2002 | Fagrell |
| 6,432,379 B1 | 8/2002 | Heung |
| 6,440,057 B1 | 8/2002 | Ergun et al. |
| 6,538,146 B2 | 3/2003 | Turck |
| 6,566,296 B2 | 5/2003 | Plantenga et al. |
| 6,596,055 B2 | 7/2003 | Cooper et al. |
| 6,656,328 B2 | 12/2003 | Kato et al. |
| 6,680,042 B1 | 1/2004 | Schulz et al. |
| 6,733,741 B2 | 5/2004 | Nakamura |
| 6,790,547 B2 | 9/2004 | Dieckmann et al. |
| 7,625,832 B2 | 12/2009 | Purta et al. |
| 2002/0060015 A1 | 5/2002 | Stivers |
| 2002/0141939 A1 | 10/2002 | Schulz et al. |
| 2003/0032826 A1 | 2/2003 | Hanna |
| 2005/0274065 A1 | 12/2005 | Portnoff et al. |
| 2008/0302703 A1 | 12/2008 | Purta et al. |

FOREIGN PATENT DOCUMENTS

| | | |
|---|---|---|
| EP | 0021242 | 1/1981 |
| EP | 0198243 | 10/1986 |
| EP | 0969110 | 1/2000 |
| EP | 1018856 | 7/2000 |
| EP | 1245534 | 10/2002 |
| GB | 795573 | 5/1958 |
| GB | 1179356 | 1/1970 |
| GB | 1563357 | 3/1980 |
| GB | 2361918 | 11/2001 |
| JP | 56081668 | 7/1981 |
| JP | 61124545 | 6/1986 |
| JP | 61295204 | 12/1986 |
| JP | 06170223 | 6/1994 |
| JP | 06-313188 | 11/1994 |
| JP | 11323466 | 11/1999 |
| JP | 2002-241326 | 8/2002 |
| SU | 791768 | 12/1980 |
| SU | 1266052 | 10/1996 |
| SU | 1638865 | 11/1996 |
| SU | 1638866 | 11/1996 |
| SU | 1638867 | 11/1996 |
| WO | 91/03281 | 3/1991 |
| WO | 00/05327 | 2/2000 |
| WO | 03/014272 | 2/2003 |

OTHER PUBLICATIONS

Peterson, G.R., et al, "Rapeseed Oil Transesterification by Heterogeneous Catalysis", Journal of the American Oil Chemists' Society, vol. 61, No. 10, pp. 1593-1597, Oct. 1984.

Berdonosov, S. S., "Mikrovolnovaya Khimiya (Microwave Chemistry)", Russian Article, Sorosovskiy Obrazovatel'Nyy Zhurnal, vol. 7, No. 1, 2001 (English Translation Attached).

Billaud, F., et al., "Catalytic Cracking of Octanoic Acid", Journal of Analytical and Applied Pyrolysis, Elsevier, pp. 605-616, 2001.

Loopy, Andre, "Solvent-Free Reactions", Topics in Current Chemistry, vol. 206, pp. 153-207, Springer-Verlag, Berlin Heidelberg, 1999.

Mazzocchia, C., et al., "Biodiesel and Fame from Triglicerides Over Acid and Basic Catalysts Assisted by Microwave", Poster Abstract from MISA 2004 Secondo Convegno Nazionale delle Microonde nell'Ingegneria e nelle Scienze Applicate, Oct. 6-8, 2004.

"Production of Hydrocarbons by Thermolysis of Vegetable Oils", Description of US4102938, Jul. 25, 1978.

Kharlamov, V. V., et al., "Hydrogenation of Cyclohexene on Different Types of Catalysts", N.D. Zelinskii Institute of Organic Chemistry, Russian Academy of Sciences, Moscow 117913, (Translated from Izvestiya Akademii Nauk, Seriya Khimicheskaya, No. 4, pp. 791-799), pp. 612-618, Apr. 1992.

Yue, An, et al., "Hydrogen Absorption Properties of Rare Earth Hydride Slurry", Journal of the Chinese Rare Earth Society, vol. 17, No. 2, Jun. 1999 (English Translation Attached), (12 pages).

Shihua, Tong, "A Review of Application of Hydrogen Storage Materials Used as Catalysts to Hydrogenation and Dehydrogenation", Materials Review, No. 5, pp. 20-24, 1994 (English Translation Attached).

Mazzocchia, C., et al., "Fast Synthesis of Biodiesel from Triglycerides in Presence of Microwaves", Advances in Microwave and Radio Frequency Processing, 8th International Conference on Microwave and High-Frequency Heating, Bayreuth, Germany, Sep. 3-7, 2001.

Saifuddin, N., "Production of Ethyl Ester (Biodiesel) from used Frying Oil: Optimization of Transesterificaction Process using Microwave Irradiation", Malaysian Journal of Chemistry, vol. 6, No. 1, pp. 77-82, 2004.

Noureddini, H., et al, "Kinetics of Transesterification of Soybean Oil", Journal of the American Oil Chemists' Society, Biocatalysis Articles, vol. 74, No. 11, pp. 1457-1463, 1997.

Canakci, Mustafa, et al, "A Pilot Plant to Produce Biodiesel from High Free Fatty Acid Feedstocks", Presented as Paper No. 016049 at the 2001 ASAE Annual International Meeting, Sacramento Convention Center, Sacramento, California, USA, Jul. 30-Aug. 1, 2001.

"Biodiesel Production and Quality", from unknown web site, Mar. 11, 2002, (4 pages).

Mazzocchia, C., et al., "Fatty Acid Methyl Esters Synthesis from Triglycerides Over Heterogeneous Catalysts in Presence of Microwaves", 3rd World Congress on Microwave and RF Applications, Sep. 22-26, 2002, (6 pages).

Zhang, Y., et al., "Biodiesel Production from Waste Cooking Oil: 1. Process Design and Technological Assessment", Bioresource Technology, vol. 89, pp. 1-16, 2003.

Knothe, Gerhard, et al., "Biodiesel: The Use of Vegetable Oils and Their Derivatives as Alternative Diesel Fuels", Fuels and Chemicals from Biomass, American Chemical Society, 1997, pp. 172-207.

Schuchardt, Ulf, et al., "Transesterification of Vegetable Oils: a Review", J. Braz. Chem. Soc., vol. 9, No. 3, pp. 199-210, 1998.

Breccia, A., et al., "Reaction Between Methanol and Commercial Seed Oils Under Microwave Irradiation", International Microwave Power Institute, 1999, pp. 3-8.

Vacek, Miroslav, et al., "Selective Enzymic Esterification of Free Fatty Acids with n-Butanol Under Microwave Irradiation and Under Classical Heating", Biotechnology Letters, vol. 22, pp. 1565-1570, 2000.

Khan, Mobashsher, et al, "Microwave-Mediated Methanolysis of Lipids and Activation of Thin-Layer Chromatographic Plates", Lipids, vol. 28, No. 10, pp. 953-955, 1993.

Banerjee, Probal, et al., "Enrichment of Saturated Fatty Acid Containing Phospholipids in Sheep Brain Serotonin Receptor Preparations: Use of Microwave Irradiation for Rapid Transesterification of Phospholipids", Biochimica et Biophysica Acta, vol. 1110, pp. 65-74, 1992.

Dasgupta, Amitava, et al., "Use of Microwave Irradiation for Rapid Transesterification of Lipids and Accelerated Synthesis of Fatty Acyl Pyrrolidides for Analysis by Gas Chromatography-Mass Spectrometry: Study of Fatty Acid Profiles of Olive Oil, Evening Primrose Oil, Fish Oils, and Phospholipids from Mango Pulp", Chemistry and Physics of Lipids, vol. 62, pp. 281-291, 1992.

Pollington, Stephen, D., et al., "The Influence of Microwaves on the Rate of Reaction of Propan-1-01 with Ethanoic Acid", Journal of Organic Chemistry, vol. 56, pp. 1313-1314, 1991.

Srivastava, Sumita, et al., "On the Synthesis and Characterization of Some New AB5 Type MmNi4.3AI0.3Mn0.4, LaNi5-xSix (x=0.1, 0.3, 0.5) and Mg-x wt% CFMmNi5-y wt% Si Hydrogen Storage Materials", International Journal of Hydrogen Energy, vol. 25, pp. 431-440, 2000.

Twaiq, Farouq, A., et al., "Catalytic Conversion of Palm Oil to Hydrocarbons: Performance of Various Zeolite Catalysts", Industrial Engineering Chemistry Research, vol. 38, pp. 3230-3237, 1999.

Lunin, V.V., et al., "Polymetallic Catalysts Derived from Intermetallic Hydrides", Journal of Molecular Catalysis, vol. 25, pp. 317-326, 1984.

Doroshenko, V.A., et al., "Investigation of Catalytic Activity of Hydrides in the Desulphurisation Reactions of Liquid Hydrocarbon Fuels", International Journal of Hydrogen Energy, vol. 21, No. 11/12, pp. 1125-1127, 1996.

Takeya, Koji, et al., "Soybean Oil Hydrogenation Using Hydrogen Storage Alloy", Novel Method of Edible Oil Hydrogenation Part III, Nippon Shokuhin Kagaku Kogaku Kaishi, vol. 43, No. 5, 1996 (English Translation Attached), pp. 502-510.

Snijder, E.D., et al., "Hydrogenation of Cyclohexene with LaNi5-xAlxHn Metal Hydrides Suspended in Cyclohexane or Ethanol", Chemical Engineering Science, vol. 48, No. 13, pp. 2429-2441, 1993.

Giguere, Raymond, J., et al., "Application of Commercial Microwave Ovens to Organic Synthesis", Tetrahedron Letters, vol. 27, No. 41, pp. 4945-4948, 1986.

Gedye, Richard, et al., "The Use of Microwave Ovens for Rapid Organic Synthesis", Tetrahedron Letters, vol. 27, No. 3, pp. 279-282, 1986.

Canakci, M., et al., "Biodiesel Production from Oils and Fats with High Free Fatty Acids", Transactions of the ASAE, vol. 44, No. 6, pp. 1429-1436, 2001.

Rohm and Haas Company, AMBERLYST A26 OH, Industrial Grade Strongly Basic Polymeric Resin, for Catalysis and Separation Technologies, Product Data Sheet, IE-631 EDS, Apr. 2001.

Soybean Oil Feed

100% conversion of the soy bean oil triglycerides

Microwave Processed Biodiesel

Yellow Grease
Oil Feed
(~18% Free Fatty Acids)

One Step Conversion of Yellow Grease Free Fatty Acids and Triglycerides

Microwave
Processed
Biodiesel

METHODS FOR PRODUCING BIODIESEL

CROSS-REFERENCE TO RELATED APPLICATIONS

This application is a continuation of U.S. patent application Ser. No. 10/867,627 filed Jun. 15, 2004, the content of which is incorporated herein by reference in its entirety.

BACKGROUND OF THE INVENTION

The use of plant oils for transportation fuel has been known for over 100 years with the use of peanut oil to power the first diesel engines. However, plant oil properties, as well as animal oil properties, are not sufficient to be a direct replacement for petroleum diesel in the diesel engines of today. The oils' viscosities are too high and do not burn clean enough, leaving damaging carbon deposits on the engine. As a result, transesterification and esterification of plant oils have been used to produce a less viscous fuel referred to as biodiesel fuel.

Significant improvements have been made over the years to the transesterification and esterification processes. However, enhancements and improvements to increase yield and reduce reaction time over existing biodiesel transesterification and esterification techniques are desired.

SUMMARY OF THE INVENTION

In one aspect, the invention may provide a method of converting feedstock having carboxylic acid and triglyceride into a biodiesel using an esterification process and a transesterification process. The method may comprise performing an esterification process including: mixing the feedstock with an alcohol to produce a reactant mixture; contacting the reactant mixture with an acid catalyst; and applying RF or microwave energy to at least one of the carboxylic acid, the alcohol, the catalyst, the mixture and a combination thereof to convert the carboxylic acid to a biodiesel. A transesterification process may also be performed to convert the triglyceride to a biodiesel.

In another aspect, the invention may provide a method of converting a triglyceride to an alkyl ester and glycerol using a transesterification process. The method may comprise mixing the triglyceride with an alcohol to produce a reactant mixture, flowing the reactant mixture over a heterogeneous catalyst with a relative velocity of at least 0.005 m/s to obtain high reactant shear at a reactant-catalyst interface and producing alkyl ester and glycerol.

In another aspect, the invention may provide another method of converting a triglyceride to an alkyl ester and glycerol using a transesterification process. The method may comprise mixing the triglyceride with an alcohol to produce a reactant mixture, emulsifying the reactant mixture with a homogeneous catalyst, applying RF or microwave energy to at least one of the triglyceride, the alcohol, the catalyst, and a combination thereof, and producing alkyl ester and glycerol.

In another aspect, the invention may provide a method of converting a carboxylic acid to an alkyl ester using an esterification process. The method may comprise mixing the carboxylic acid with an alcohol to produce a reactant mixture, contacting the reactant mixture with an acid catalyst and applying RF or microwave energy to at least one of the carboxylic acid, the alcohol, the catalyst and a combination thereof to produce an alkyl ester.

In another aspect, the invention may provide a method of converting a carboxylic acid to an alkyl ester using an esterification process. The method may comprise mixing the carboxylic acid with an alcohol to produce a reactant mixture, flowing the reactant mixture over a heterogeneous acid catalyst with a relative velocity of at least 0.005 m/s to obtain high reactant shear at a reactant-catalyst interface, and producing alkyl ester.

In another aspect, the invention may provide a method of converting a carboxylic acid to an alkyl ester using an esterification process. The method may comprise mixing the carboxylic acid with an alcohol to produce a reactant mixture, emulsifying the reactant mixture with a homogeneous acid catalyst, applying RF or microwave energy to at least one of the carboxylic acid, the alcohol, the catalyst, and a combination thereof, and producing alkyl ester.

DETAILED DESCRIPTION OF THE INVENTION

Figure 1:
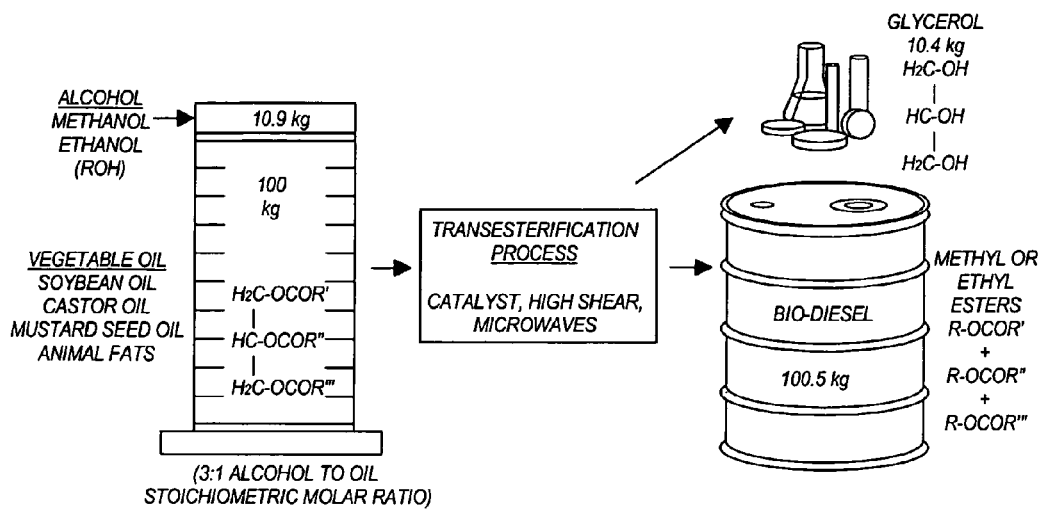
FIG. 1 shows a biodiesel transesterification production process embodying the invention.

The invention relates individually to a transesterification and esterification process, including a two-step esterification-transesterification process. Collectively, these are the "conversion processes". These reactions use oils comprising carboxylic acids (e.g., free fatty acids (FFAs)), triglycerides (TGs), or a mixture thereof, in combination with alcohol, to produce biodiesel fuels comprising fatty acid alkyl esters (FAAEs) and glycerol or water. More specifically, the triglycerides can be converted using transesterification to produce FAAEs (e.g., biodiesel) and glycerol, and free fatty acids can be converted using esterification to produce FAAEs (e.g., biodiesel) and water. Complex oils having both triglyceride and FFAs may undergo a one step or two-step esterification-transesterification process to produce FAAEs, glycerol, and water. The details of the present invention are described below using the following terminology.

As used herein, "oil" may refer to plant oil, animal oil or fats, waste oil or greases, rendered product, or any mixture thereof.

As used herein, the term "plant oil" is meant to refer to lipids derived from plant sources, such as agricultural crops and forest products, as well as wastes, effluents and residues from the processing of such materials, such as soapstock. Examples of plant oils include, but are not limited to, oils derived from soybeans, corn, sunflower, palm, nut, safflower, olives, cotton, linseed, mustard seed, rapeseed, canola, peanuts, coconut, castor beans, tall oil and combinations thereof.

As used herein, the term "animal oil" is meant to refer to lipids derived from animal sources, as well as wastes, effluents and residues from the processing of such materials. Examples of animal oils include, but are not limited to, raw or rendered animal fats, brown grease, white grease, yellow grease, animal tallow, pork fats, pork oils, chicken fats, chicken oils, mutton fats, mutton oils, beef fats, beef oils, and combinations thereof.

As used herein, the term "rendered product" is meant to refer to a fat that has been treated, usually with heat, to remove water, solids, and other impurities.

As used herein, the term "alcohol" is meant to refer to a hydrocarbon compound containing one or more hydroxy groups, and includes anhydrous alcohols such as methanol, ethanol, propanol, and butanol.

As used herein, "carboxylic acid" is meant to refer to an organic acid containing one or more carboxylic acid groups within its carbon structure. A carboxylic acid group contains a carbon atom with a double bond to an oxygen atom and a single bond to a hydroxy group.

As used herein, the term "free fatty acid" is meant to refer to organic acids synthesized in nature by both animals and plants and may be abbreviated "FFA." Fatty acids typically contain a hydrocarbon group with 14 to 24 carbon atoms, possibly in a straight chain, although chains of 4 to 28 carbons may be found. Longer chains exist, but typically in low concentrations. The fatty acid may be in the neutral or in the anionic form. Fatty acids are a species of carboxylic acids. Free fatty acids are used to describe fatty acids that are not bound in an ester compound.

As used herein, the term "triglyceride" is meant to refer to a triple ester of glycerol with three fatty acids, and may be abbreviated "TG."

As used herein, the term "esterification" is meant to refer to a process of producing an alkyl ester by reaction of an alcohol with a carboxylic acid.

As used herein, the term "transesterification" is meant to refer to the reaction between an ester and an alcohol with exchange of alkoxyl or acyl groups to form an alkyl ester.

As used herein, the term "biodiesel" is meant to refer to fatty acid alkyl esters used as a transportation and power generation fuel.

As used herein, "fatty acid alkyl esters" are meant to refer to esters composed of a fatty acid group and an alkoxy group, and may be abbreviated "FAAEs."

As used herein, applying "high shear conditions" is meant to refer to high tangential fluid velocity of reactants over or at a catalyst interface.

As used herein, "emulsification" is meant to refer to the process of dispersing droplets of one liquid into another, immiscible liquid. High shear mixing (or flow) can be used to prepare an emulsion.

As used herein, "emulsion" is meant to refer to the result of dispersing droplets of one immiscible liquid into another. In an emulsion the droplets may range in diameter from 0.001 to 1000 micrometers.

As used herein, "autogeneous condition" or "autogeneous pressure" is meant to refer to the sum of all reactant and product equilibrium partial pressures at a given temperature.

As used herein, "heterogeneous catalyst" is meant to refer to a catalyst that is in a different phase from the reactants, and may include both acid and alkaline catalysts, as well as immobilized enzyme catalysts.

As used herein, "homogeneous catalyst" is meant to refer to a catalyst that is in the same phase as the reactants, and may include both acid and alkaline catalysts.

As used herein, "LHSV" is meant to refer to liquid hourly space velocity. LHSV is defined as the ratio of the hourly volumetric flow rate to the volume of catalyst. LHSV is used to describe the contact time between the reactant and the catalyst for heterogeneous catalysis.

As used herein, "WHSV" is meant to refer to weight hourly space velocity. WHSV is defined as the ratio of the weight of reactants to the weight of catalyst in reaction per hour. WHSV is used to describe the process time of the reactant and the catalyst for homogeneous catalysis.

As used herein, "dielectric loss tangent" is meant to refer to the dielectric parameter called the loss tangent. This parameter is known by those skilled in the art to measure the relative RF or microwave energy that a particular material absorbs at a given frequency. The loss tangent, also called the loss factor, is the ratio of the energy lost to the energy stored. A larger loss tangent for a material means that more energy is absorbed relative to a material with a lower loss tangent. The dielectric absorption of energy can cause different materials to heat at substantially different rates and to achieve considerably different temperatures within the same RF or microwave field.

The three main processes of the present invention, transesterification, esterification, and esterification-transesterification (both one-step and two-step) are described below with reference to the accompanying figures.

Transesterification

FIG. 1 shows a transesterification process diagram that is used to illustrate certain aspects of the present invention. In FIG. 1, an alcohol and an oil comprising triglycerides are mixed and used as feedstock for the transesterification process. Typically, oils comprising triglycerides and having less than one weight percent free fatty acids are used for transesterification. In the transesterification process, the reaction of the alcohol and oil is catalyzed to produce biodiesel, fatty acid alkyl esters, and glycerol. In FIG. 1, the ratio of the reactants is pictorially represented at stoichiometric molar ratios. Three moles of alcohol are needed to react with one mole of triglycerides. Thus, under ideal conditions, for complete triglyceride conversion to biodiesel, the alcohol required is over 10 wt % of the triglyceride reactant. The details of the illustrated process are described below with reference to FIG. 2.

Figure 2:
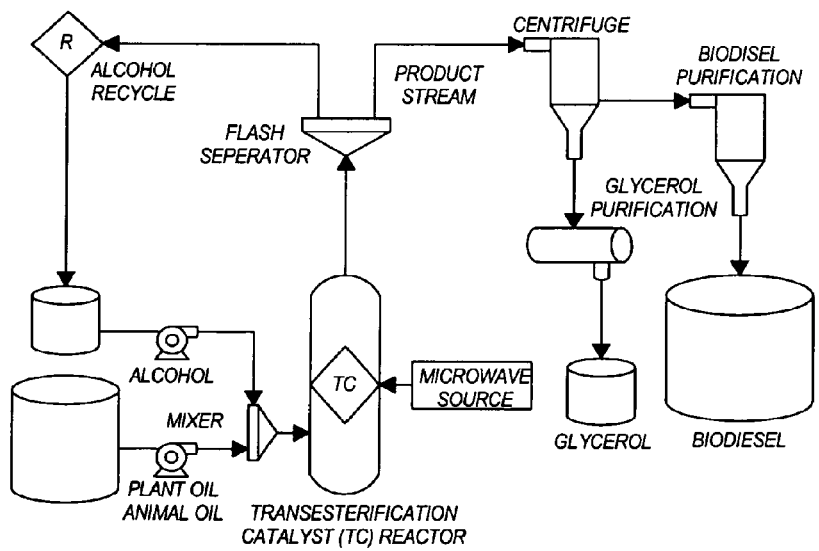
FIG. 2 shows a flow chart of a transesterification process embodying the invention.

FIG. 2 schematically illustrates each of the components of the transesterification process. In the illustrated embodiment, alcohol and oil sources feed into a mixer, where the alcohol and oil are mixed before being fed into the catalyst reactor. Alternatively, the alcohol and oil may be introduced directly into the catalyst reactor, and be mixed concurrently as each reactant contacts the catalyst. The molar ratio of alcohol to oil in the reactions may range from the stoichiometric ratio of 3:1 to 60:1, although ratios of 4:1 to 20:1 are more typical. The methanol in excess of the stoichiometric ratio is known to help the reversible transesterification reaction to proceed in the direction of producing biodiesel.

The catalyst reactor can be any of a number of different types. For example, it could be a fixed bed reactor, a continuous stirred batch reactor, a slurry bed reactor, or any other suitable reactor. The chosen type of reactor will depend on the desired process conditions, as is known in the art.

The product leaving the catalyst reactor enters a separator that removes excess alcohol from the stream, which is recycled to the reactor. The product is then sent to a centrifuge for separation of the product into glycerol and biodiesel. The glycerol and biodiesel may undergo subsequent purification processes understood by those in the art to produce a commercially useful end product.

In an alternative embodiment (not shown), when used with a homogeneous catalyst, the product stream may be sent through an ion exchange bed before product separation. The ion exchange bed removes the homogeneous catalyst from the product stream without the need for real time neutralization. Ion exchange beds are more applicable to continuous processes than are alternative neutralization and catalyst removal techniques. The ion exchange bed can be composed of resins in the hydrogen form (e.g. Amberlite IR resins from Rohm and Hass) or the hydroxide form (e.g. Amberlite IRA resins from Rohm and Hass) depending on whether the homogeneous catalyst is a base or an acid. More particularly, the product stream comprising alcohol, fatty acid alkyl esters, and glycerol may be separated and the fraction containing the alcohol and glycerol sent through an ion exchange bed to remove acid ions. Microwaves may optionally be applied to enhance alcohol flash separation and as a pretreatment for FAAE and glycerol separation. The FAAE and glycerol may be separated using centrifugation (with or without microwave application). The FAAE and glycerol components may then be further purified for commercial use.

In another embodiment (not shown), the product separation may be performed using a different methodology before an ion exchange bed is used. If the catalyst operates below the alcohol boiling point at reaction conditions, microwaves may be applied for enhanced alcohol flash separation. If the catalyst operates above the alcohol boiling point at reaction conditions, flash separation of alcohol may occur without microwaves. The FAAE and glycerol may be separated using centrifugation (with or without microwave application). The FAAE may be washed with water or alcohol to remove ions. The wash from FAAE may be combined with glycerol, and the mixture may be sent through an ion exchange bed. The glycerol may be sent through a microwave enhanced flash separation unit. Again, the FAAEs and the glycerol components may be further purified for commercial use.

The transesterification process, as well as the other conversion processes discussed herein, may be enhanced by one or more of the following: 1) applying microwave or RF energy; 2) passing reactants over a heterogeneous catalyst at sufficiently high velocity to achieve high shear conditions; 3) emulsifying reactants with a homogeneous catalyst; or 4) maintaining the reaction at a pressure at or above autogeneous pressure. Enhanced processes using one or more of these steps can result in higher process rates, higher conversion levels, or both.

Microwave or radio frequency (RF) electromagnetic energy (1000 m to $10^{-4}$ m wavelength) can be applied to the reactants, catalysts, or mixtures thereof, either in the absence or presence of fuel-fired heating or resistive heating. The microwave energy or RF can provide for a significant increase in process rates, higher conversion levels, or both compared to conventional heating because it tends to activate the ionic catalyst site. More specifically, the catalyst is designed to be an absorber of microwave energy, thereby facilitating the heating of the location where the reactions occur. MW energy selectively energizes the catalyst's interaction with the reactants. Consequently, a smaller ratio of alcohol to free fatty acid/triglyceride may be used, while still obtaining higher FFA/TG process rates. Additionally lower bulk process temperatures can be utilized.

In order to control and optimize reaction exchange, the microwave frequency, power density, and field strength, can be controlled. Suitable control of these parameters influences the reaction between the catalyst and the reactants. Furthermore the use of microwave energy can minimize secondary reactions and bring about complete conversion of the reactants.

The frequency of the microwave or RF energy may be selected to achieve high conversion of the reactants and still utilize a commercially available high power microwave source. The microwave dielectric parameters and energy absorption of plant oils and biodiesel have been characterized over the range of 0.6 to 6 GHz. The dielectric parameters and in particular the loss tangent which governs the microwave power absorption, can be shown to be nearly flat and independent of frequency for plant oils and biodiesel. These characterizations have shown that microwave absorption is sufficiently uniform that microwave energy is useful both within this frequency range and one skilled in the art can easily extrapolate that microwaves will be equally useful well outside of this range. For example, very high power, microwave sources, at 915 MHz and 2.45 GHz, are commercially available within the United States (other countries assign different high power microwave sources frequencies). Conversion rates are anticipated to be relatively independent of microwave frequency. A portion of the RF or microwave frequency can be between about 1 MHz and about 100 GHz, more particularly, between about 100 MHz and about 10 GHz, and even more particularly, between about 400 MHz and about 5 GHz. Lower frequencies have longer wavelengths and therefore have greater penetration depth into the catalyst and reactants, which allows the design of physically larger reactors. Lower frequencies, such as 915 MHz, are more suitable for larger, higher power reactors because higher power low, frequency generators are commercially available.

The power density also may be controlled to enhance conversion. In one embodiment, the average power density is controlled between about 0.01 watts/cc and about 100 watts/cc, and particularly, between about 0.05 watts/cc and about 10 watts/cc, and even more particularly, between about 0.1 watts/cc and about 3 watts/cc.

Continuous wave or modulation methods can be used to control microwave energy. Continuous wave involves the application of microwave energy at a constant amplitude. *Modulation techniques may include amplitude modulation, frequency modulation, pulse width or duty cycle modulation, or combinations thereof. The use of modulation can result in high peak microwave power compared to average power and greater temperature differentials between the catalyst and the* reactants. By control of modulation, such as the microwave power's duty cycle, the catalyst can be differentially heated and cooled. With a porous catalyst, this can result in enhanced diffusion of the reactants and products as the catalyst is heated and cooled, encouraging higher reaction rates at lower bulk operating temperatures. For some applications, high peak fields and lower average power may enhance reaction rates or product separation.

It may be cost-effective to maximize the use of fossil fuels to pre-heat the feedstocks to near reaction temperatures, and use minimum RF or microwave energy to drive and control the reactions. In some embodiments, there may be a minimized or zero net temperature increase from the RF or microwave energy into the catalyst. Selective coupling of the RF or microwave energy is accomplished through selection and control of the relative dielectric parameters of the catalyst's components and the feedstock. This results in efficient, economically-viable catalytic processes, which are enhanced using RF or microwaves. Using microwave or RF energy may activate the catalyst site, enhance diffusion and removal of products from the catalytic site, and promote rapid separation and elimination of emulsions.

In order to enhance the catalytic reaction using a heterogeneous catalyst, the catalyst is subjected to the reactant's high shear fluid flow conditions. More specifically, the reactants are brought into contact with a heterogeneous catalyst at a high relative velocity. These high shear conditions have been observed to improve the reaction time and reactant conversion. Consequently, a smaller ratio of alcohol to free fatty acid/triglyceride and/or higher FFA/TG process rates, LHSV or WHSV, may be used. High shear conditions occur when the reactants are brought into contact with a heterogeneous catalyst at a velocity of greater than about 0.001 m/s, and more particularly, a velocity of greater than about 0.05 m/s. Typically, the reactants flow at velocity of less than about 0.5 m/s, and more particularly, less than about 0.25 m/s.

Using such high shear conditions with a heterogeneous catalyst, 100 percent conversion of triglycerides may be achieved in a shorter period of time, purification steps can be reduced, and acid neutralization steps may be eliminated. This improvement results in an increase in LHSV values in the range of about 30, 45, or 60 or more for 100% conversion. It is believed that the high shear conditions shift the equilibrium of the reversible transesterification reaction to the product side by providing short catalyst contact time with the reactants and products.

When using a homogeneous catalyst, the reaction can be enhanced by emulsifying the feed oil with a solution comprised of the alcohol and the dissolved catalyst. This can be accomplished by dissolving the homogeneous catalyst into the alcohol phase. The catalyst-alcohol solution is then combined with the feed (FFA, TG, or mixture) and into an emulsifying system, such as through a high shear gear pump or other high shear mixing methods. Emulsification enhances intimate contact and mixing of the reactants prior to reaction. The respective surface area of the reactants increases as the emulsion droplet size decreases. The larger the droplet sizes, the more likely the suspended droplets will eventually agglomerate and immiscible liquids separate. Respectively, the smaller the droplet size the more likely the emulsion will not separate and will remain a stable mixture. The microwave energy further enhances the reaction through selective heating. Given an emulsion of alcohol, with dissolved catalyst (e.g. NaOH), and triglyceride phases, the microwave will be preferentially absorbed by the alcohol phase raising its temperature, thereby increasing the catalyst reaction rate. Acid and base catalysts dissolved in the alcohol phase also further increase the microwave absorption.

Controlling the pressure at which the methods are conducted may also enhance conversion. Particularly, keeping the reaction pressure at or above autogeneous pressure keeps the alcohol reactant in liquid phase to enhance reactions. This can be done by pressurizing the system hardware with air or an inert gas such as nitrogen. One way to determine an appropriate system hardware pressure is to total the pressure drops through out the hardware, for example the pressure drop across the catalyst bed, and to add the autogeneous pressure to this value. This is the minimum pressure requirement to prevent pump cavitations. The operating hardware system pressure should then be set at or above this total. Another way to set system pressure is to pre-pressurize the system hardware when at ambient temperature, for example 10-60 psig. Operating pressures above autogeneous conditions also allows for lower alcohol to FFA/TG molar ratios. In some embodiments, the pressure is maintained at or above about 5 psig above autogeneous, and more particularly, at or above about 10 psig above autogeneous pressure. Typically, the pressure will be maintained below about 100 psig above the autogeneous pressure, and more particularly, at or below about 50 psig above autogeneous pressure.

Transesterification reactions may employ both heterogeneous catalysts, homogeneous catalysts and combinations thereof. In addition, the catalyst for transesterification reactions may be alkaline or acidic.

Examples of alkaline heterogeneous catalysts include, but are not limited to, at least one of a hydroxide of Group 1 or 2 metals, a silicate of Group 1 or 2 metals, a carbonate of Group 1 or 2 metals, a strong anion exchange resin in the hydroxide form, an oxide of aluminum and magnesium, and mixtures thereof. Particularly, Dowex 550A commercially available from the Dow Chemical Company, Amberlyst A26(OH) commercially available from the Rohm and Haas Company may be used.

Alkaline heterogeneous catalysis may yield high purity products without requiring neutralization or water washing. Although a variety of the process parameters defined above may be used, high velocity (e.g., about 0.004 m/s to about 0.350 m/s), low to moderate temperature (e.g., about 40-150° C.), low to moderate pressures (e.g., autogeneous pressure to about 50 psig above) and low to moderate alcohol to oil molar ratios (e.g., 3:1 to 20:1) are expected to yield high conversions. These same conditions apply to acid heterogeneous catalysis discussed in more detail below.

Examples of acid heterogeneous catalysts include, but are not limited to, zeolite in the acid form, a strong cation exchange resin in the hydrogen form, Lewis acids and combinations thereof. Particularly, Dowex DR-2030 commercially available from the Dow Chemical Company, Amberlyst 36 commercially available from the Rohm and Haas Company, ZSM-5 commercially available from UOP, or Zeolyst International, USY commercially available from Tosoh Corporation, and combinations thereof may be used. The supports discussed above can be used for the acid catalysts.

While the parameters given above may be used, high velocity (e.g., about 0.004 m/s to about 0.35 m/s), low to moderate temperatures (e.g., about 65-150° C.), low to moderate pressures (e.g., autogeneous pressure to about 50 psig there above), and low to moderate alcohol to oil ratios (e.g., 3:1 to 20:1 molar) are anticipated to achieve good results.

Heterogeneous catalyst can be made entirely of the acid or base compound or it can be dispersed or coated onto a support material such as an inert substrate. The substrate can also comprise a microwave absorber and an inert substrate. Surface area affects the reactivity per unit volume of catalyst and thereby increases the process reaction rates. In order to increase the surface area of the active catalytic elements, the catalyst may be coated onto a support material. The support also provides for controlling the pressure drop across the catalyst bed and for ease of handling.

The proper control and use of the dielectric loss tangent in the catalyst support leads to the efficient use of microwave energy. The loss tangent, also called loss factor or the dissipation factor, is a measure of the material's microwave adsorption. The fraction of microwave energy, which is absorbed by any component, e.g. oil, catalyst or catalyst component, can be efficiently controlled. For example, when the dielectric loss tangent of the catalyst is equal to the oil, then approximately half the microwave energy initially goes into heating the oil and half into the catalyst. The primary method of loss tangent control is by adjusting the material compositions of the individual components. This includes the optimization of catalyst composition or the blending of feedstocks.

The supports may be amorphous or crystalline and may have differing dielectric loss tangents. More particularly, the loss tangent may be greater than about 0.01, and even more particularly, greater than about 0.05. The loss tangent typically is less than about 0.5, and particularly, less than about 0.3. If the support is itself transparent to microwave or RF frequencies, an additional dielectric material may be added to the catalyst system in order to increase energy absorption. The support may be a carbon or carbide material such as silicon carbide. It may also be a silica or alumina material, or an aluminosilicate such as a zeolite. Other metal oxides, such as calcium oxide or magnesium oxide, may also be used. In one embodiment, the combination of the catalyst and alcohol absorb more than 50% of the microwave energy by selection of the catalyst's dielectric properties.

Examples of alkaline homogeneous catalysts include, but are not limited to sodium or potassium hydroxide, C1 to C6 alkoxide, and combinations thereof. Concentrations of homogeneous catalysts may include a range of 100 ppm to 5 wt %. The alkaline catalysts act as excellent microwave absorbers, the activity of which is greatly enhanced by microwaves. Concentrations from 0.02 wt % to 2.00 wt % may be used, along with higher concentrations. The reaction may occur below the boiling point of alcohol.

Examples of acid homogeneous catalysts include, but are not limited to, sulfuric acid, nitric acid, phosphoric acid, hydrochloric acid, and combinations thereof. The acid catalysts are excellent microwave absorbers and the activity of which is greatly enhanced by microwaves. Concentrations from 0.05 wt % to 5.00 wt % may be used, while higher concentrations can also be used.

The preferred process embodiment for transesterification is to first dissolve the homogeneous catalyst into the alcohol phase and combine this solution with the feed (FFA, TG, or mixture) into an emulsifier system, such as a high shear gear pump. The emulsified mixture is then pumped through a flow through microwave reactor. The feed can be pre-heated, either before or after emulsification, using conventional heat so the microwave energy is used primarily for catalyst activity enhancement. Microwave energy from 0.05 W/cc to 10 W/cc is applied to the emulsified reactants. Process parameters include low to moderate temperature (e.g., about 40-150° C.), low to moderate pressures (e.g., autogeneous pressure to about 50 psig above) and low to moderate alcohol to oil molar ratios (e.g., 3:1 to 20:1) are expected to yield high conversions. These same conditions apply to acid homogeneous catalysis discussed in more detail below. Operating temperatures between 60 and 90° C. are preferred for a base homogeneous catalyst and between 100 and 150° C. are preferred for an acid homogeneous catalyst since there is a diminishing advantage to using higher temperatures.

The increased reaction rates and conversions to 100%, achieved using emulsification and microwave energy, allow for the use of lower catalyst concentrations. For example, catalyst concentrations on the order of 0.01 to 1 wt % lower catalyst and neutralization costs, including the economical use of ion-exchange systems used in continuous process flow systems.

Esterification

Figure 3:
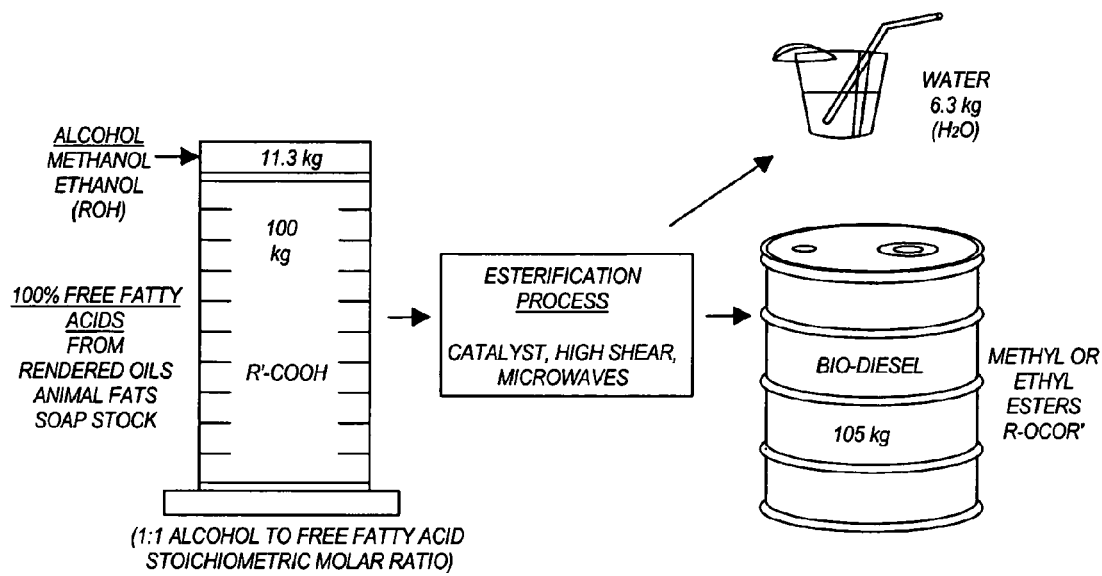
FIG. 3 shows a biodiesel esterification production process embodying the invention.

FIG. 3 shows an esterification process diagram that is used to illustrate certain aspects of the present invention. In FIG. 3, an alcohol and a feedstock, like rendered oils, animal fats, or soap stock, with free fatty acids, are mixed and used as reactants for the esterification process. The ratio of the reactants is pictorially represented at stoichiometric molar ratios, and the free fatty acid concentration is 100%. One mole of alcohol is needed to react with one mole of free fatty acids. Thus, under ideal conditions, for complete FFA conversion to biodiesel, the alcohol required is over 11 wt % of the free fatty acid reactant. Typically, the free fatty acids in the feedstock will comprise at least about 1 wt % free fatty acids, more particularly, greater than about 5 wt %, and even more particularly, greater than about 10 wt %. The free fatty acid contents are mixed with an alcohol. Acid catalysts, both heterogeneous, homogeneous and combinations thereof, can be used in the esterification reactions to produce alkyl esters and water. These acid catalysts are the same as those set forth and discussed in more detail above with regard to transesterification. The same process parameters, as set forth above with respect to the transesterification reactions, can be used to enhance the esterification conversion reactions. Particularly, the esterification processes may be enhanced by applying microwave or RF energy, applying high shear conditions with a heterogeneous catalyst, emulsifying reactants with a homogeneous catalyst, and maintaining the reaction at a pressure at or above autogeneous pressure. Similar separation and purification techniques as given for transesterification may also be used with the addition of a flash separator to remove the water produced.

In one example of esterification, heterogeneous acid catalysis may be used to convert oils having greater than about 90% free fatty acids and an alcohol. The free fatty acids and the alcohol contact the heterogeneous acid catalyst during or after the FFAs are mixed with the alcohol to form a FFA-alcohol mixture. Again, any of the process parameters as quantified for heterogeneous catalysis above may be used. Similarly, high velocity (e.g., about 0.004 m/s to about 0.35 m/s), low to moderate temperature (e.g., about 40-150° C.), low to moderate pressures (e.g., autogeneous pressure to about 50 psig there above) and low to moderate alcohol to oil ratios (e.g., 3:1 to 20:1 molar) are expected to yield high conversions. The microwave conditions discussed above may be used for this type of catalysis as well. Again, any of the process parameters as quantified for homogeneous catalysis above may be used. Similarly microwave power density (e.g. 0.01 W/cc-10 W/cc), low to moderate temperature (e.g., about 40-150° C.), low to moderate pressures (e.g., autogeneous pressure to about 50 psi there above) and low to moderate alcohol to oil ratios (e.g., 3:1 to 20:1 molar), in addition to the use of emulsification are expected to yield high conversions.

Esterification-Transesterification

Figure 4:
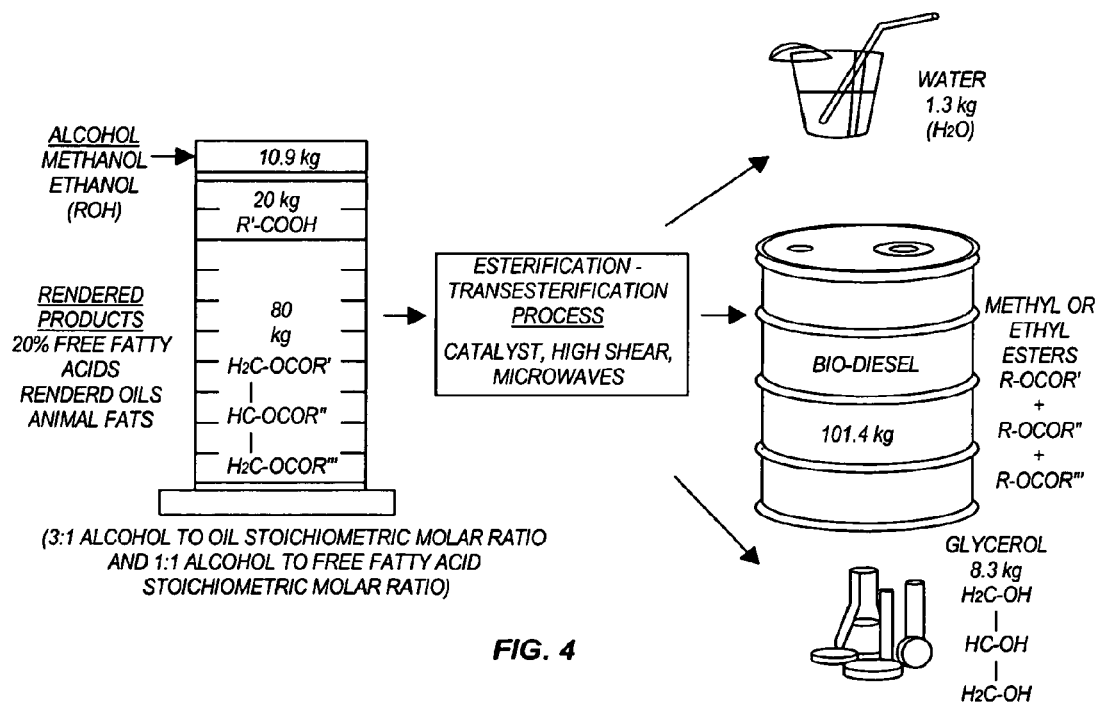
FIG. 4 shows a biodiesel esterification-transesterification production process embodying the invention.

FIG. 4 shows a simplified esterification-transesterification process diagram that is used to illustrate certain aspects of the present invention. In FIG. 4, an alcohol and a feedstock, like rendered oils, animal fats, or soap stock, with free fatty acids, are mixed and used as reactants for the esterification-transesterification process. The ratio of the reactants is pictorially represented at stoichiometric molar ratios, and the free fatty acid concentration is 20%. Typically, the free fatty acids in the feedstock will comprise at least about 1 wt % free fatty acids, more particularly, greater than about 5 wt %, and even more particularly, greater than about 10 wt %.

Acid catalysts, both heterogeneous, homogeneous and combinations thereof, can be used in the esterification-transesterification reactions to produce biodiesel (i.e. fatty acid alkyl esters), glycerol and water. These acid catalysts are the same as those set forth and discussed in more detail above with regard to esterification-transesterification. The same process parameters, as set forth above with respect to the transesterification reactions, can be used to enhance the esterification-transesterification conversion reactions. Particularly, the esterification-transesterification processes may be enhanced by applying microwave or RF energy, applying high shear conditions with a heterogeneous catalyst, emulsifying reactants with a homogeneous catalyst, and maintaining the reaction at a pressure at or above autogeneous pressure. Similar separation and purification techniques as given for transesterification may also be used with the addition of a flash separator to remove the water produced.

Figure 5:
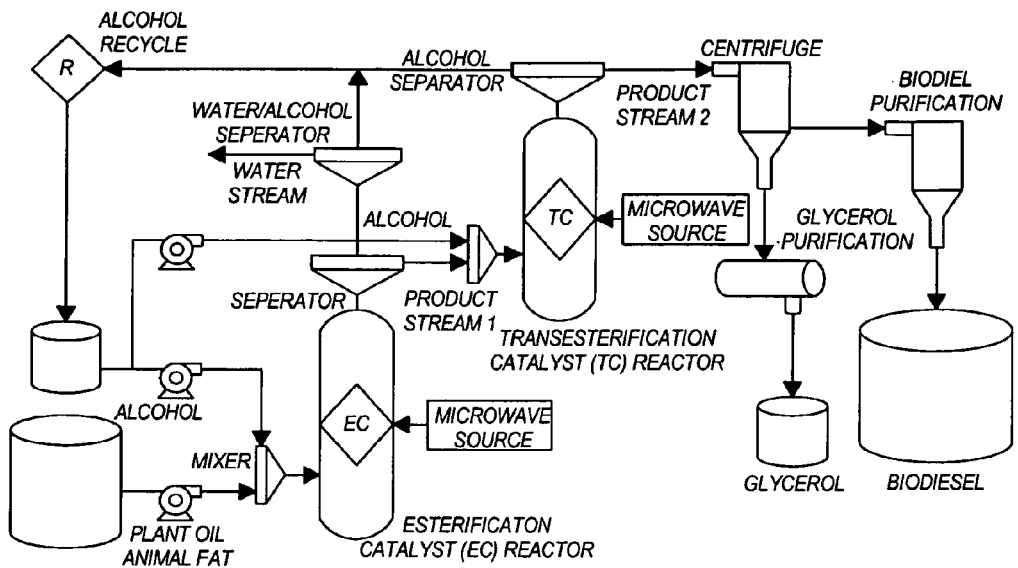
FIG. 5 shows a flow chart of a two-step esterification-transesterification process embodying the invention.

FIG. 5 schematically illustrates each of the components of a two-step esterification-transesterification process. If the oil contains more than about 1% by weight free fatty acids, then the two-step process is preferred. Rendered products having up to about 10% free fatty acids, and more particularly, up to about 20% by weight free fatty acids may be used.

In the illustrated embodiment, oil sources containing triglycerides and free fatty acids (TG/FAA), and alcohol are fed into a mixer, where the alcohol and TG/FAA are mixed before being fed into the esterification catalytic reactor. Alternatively, the reactants may directly be introduced into the esterification reactor. The esterification reactor includes one of the acid catalysts, either heterogeneous or homogeneous, discussed previously. The first step converts the free fatty acids into FAAE and water.

The product leaving the esterification reactor enters a separator, where alcohol is recycled and water is removed. The product stream from the esterification reactor, containing unprocessed triglycerides and FAAE, and alcohol are fed into a mixer before being fed into the transesterification catalytic reactor. Alternatively, the reactants may be introduced directly into the transesterification reactor.

The second step, transesterification, takes place in the transesterification reactor, with the assistance of one of the alkaline or acid catalysts, either heterogeneous or homogeneous, set forth above, and converts the triglycerides into biodiesel (i.e. FAAE) and glycerol. The product leaving the transesterification reactor enters a separator, where alcohol is recycled and the product stream, containing biodiesel and glycerol, is subsequently separated, optionally by centrifugation, and purified to yield biodiesel and glycerol as illustrated with respect to the transesterification process shown in FIG. 5.

Similar to the other conversion processes described previously, the two-stage conversion processes may be enhanced by applying microwave or RF energy, applying high shear conditions with a heterogeneous catalyst, emulsifying reactants with a homogeneous catalyst, maintaining the reaction at a pressure at or above autogeneous pressure, or any combination thereof. Either or both of the esterification and transesterification processes may use these techniques. The parameters defined previously may be employed with these conversion reactions.

Numerous combinations of the two-step conversion exist, each having its own commercial value. For example, the esterification step can be performed using an acid catalyst that is either heterogeneous or homogeneous. In addition, the transesterification step can be performed using either an acid or a base catalyst that is either heterogeneous or homogeneous.

Additionally, an integrated esterification-transesterification process can take place in a single reactor using an acid catalyst, either homogeneous or heterogeneous.

EXAMPLES

Example 1

Figure 6:
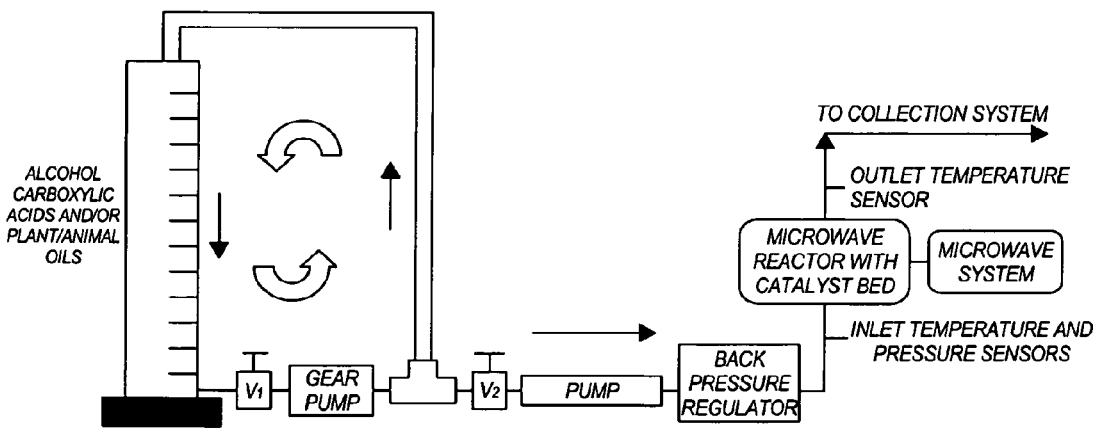
FIG. 6 is a microwave fixed bed test system embodying the invention.

Effect of Increasing Feed Velocity, with Fixed Bed Reactor, on Alkaline Heterogeneous Transesterification A fixed bed reactor was set up to operate with microwave power as shown in FIG. 6. The illustrated system includes a cylinder, a high-shear gear pump, and a return line that maintain the reactants as a mixed emulsion. The reactants are maintained as an emulsion by passing the reactants through the high shear gear pump at ambient temperature and pressure and returning the emulsion to the holding cylinder.

A valve $V_2$, a second pump, and a backpressure regulator control the flow rate of the emulsified reactants through the catalyst bed, contained in the microwave flow-through reactor system. The microwave generating system comprises a 0 through 25 Watt microwave source (Sairem, GMM.25.2450), power meter (Anritsu, ML2438A), BNC to WR284 waveguide adapter (Lectronic Research Labs), EH tuner (FXR Inc, S312B), dual directional coupler (Mac, 31145B-50), and associated microwave coax cables and connectors. The use of the EH tuner and dual directional coupler are known to those skilled in the art to maximize the coupling of the microwave energy into the catalyst reactor.

A water load (Richardson Electronics, P#WR284LOAD6A) was modified with stainless steel screens (200 mesh) and Buna N or Viton O-Rings to make a flow through catalyst bed able to handle temperatures to 100° C. and pressures to 150 psig.

The products of the reaction were sent to a collection/separation system for later analysis.

Tests were run under the following test conditions: 65° C., autogeneous pressure, 6:1 methanol to soybean oil ("SBO") molar ratio, 0.5 W/cc power density, 2.45 GHz frequency, continuous wave (CW) microwave, and 10 cc catalyst bed volume, and heterogeneous alkaline catalyst, sodium silicate (Alfa Aesar, 14106). Samples were collected and evaluated for two flow rates, 2 and 4 ccm, equivalent to LHSV of 12 and 24. The liquid velocity through the catalyst bed was calculated to be 3.47E-04 m/s at the flow of 2 ccm and 6.93E-4 m/s at a flow of 4 ccm. The system was operated from 2-30 minutes for each test condition. The conversion rate was measured by gas chromatographic analysis of feed and product.

It was expected that with the lower the LHSV test conditions, the conversion rates would be higher due to the longer residence time of the reactants in the reactor. In this case, surprisingly, the opposite was observed. The triglycerides (TG) conversion rate was 64% at LHSV 24 and 31% at LHSV 12. Consequently, the lower the LHSV, the lower the conversion of TGs, while the higher the LHSV, the higher the conversion.

This observation lead to unique and non-obvious deductions that for esterification and transesterification heterogeneous reactions, high velocity flow rates provided the means for higher levels of conversion at higher process rates.

Set up for Continuous Stirred Batch (CSB) Reactor for Examples 2-7 & 19-21

Figure 7:
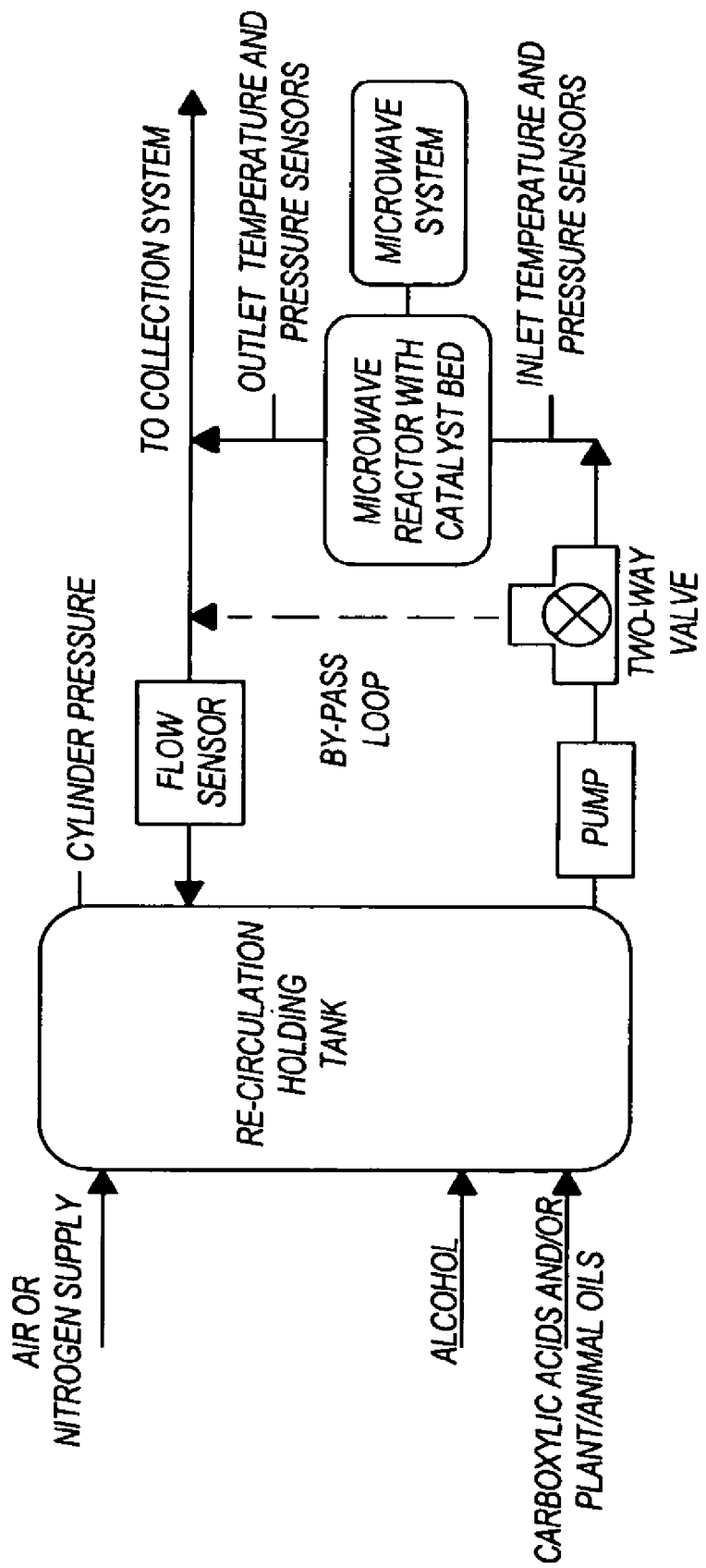
FIG. 7 is a continuous stirred batch reactor system embodying the invention.

This system was designed to investigate the effect of microwaves, flow velocity, temperature, pressure, and catalyst composition on the conversion of free fatty acids and triglycerides. As shown in FIG. 7, this system comprises a re-circulation holding tank, a high-speed pump, and a microwave, flow-through, catalyst bed reactor. The microwave system controls and monitors microwave input power and modulation. The tanks, lines, pump, and catalyst bed are all heated conventionally with temperature controlled heat tape. Pressure and temperatures sensors are placed in the system to monitor reaction conditions.

The microwave system can provide 2.45 GHz microwave energy in continuous wave mode or pulsed mode. Unless specified it is understood that continuous wave mode was selected. If pulse mode was selected, the 2.45 GHz microwave energy was modulated using a 50% on-off duty cycle with a period of 10 Hz.

The system can operate with conventional heat alone or with the addition of microwave energy into the catalyst bed. A by-pass loop was installed to allow the alcohol/oil mixture to reach temperature before being exposed to the catalyst.

For a typical test, the alcohol, oil or mixture thereof was fed into the re-circulation holding tank. The system was charged with either 300 or 350 cc of feed. The two-way valve was turned so the mixture moved through the by-pass loop. The pump and heaters were turned on and the mixtures were allowed to mix and equilibrate at operating temperature. At that time, a sample was collected and the two-way valve was turned to allow the mixture to flow through the catalyst bed. This was considered the time zero of the test. Samples were collected periodically until the test was ended. The temperature, pressure, flow rate, and microwave power data were collected and recorded for each sample. A mass balance was also performed for each example.

Tests were performed at pressures of 10 to 60 psig above autogeneous pressure. This was achieved by pressurizing the system using pressurized air or nitrogen to a preset pressure (i.e. 10-60 psig), after the reactants were fed into the system and pump started. Using pressures above the autogeneous pressure was done to minimize the alcohol in the vapor phase, to prevent pump cavitations, and to achieve predictable process control.

For all gas chromatograph analysis the following GC was used: Perkin-Elmer Autosystem XL GC equipped with a FID detector, a 10 m, 0.53 mm id, MXT-2887 Silcosteel-treated stainless steel capillary column manufactured by Restek, operated with oven temperature from 40 to 360° C.

Example 2

Demonstration of Heterogeneous Transesterification

Using the CSB system described in FIG. 7, 10 cc of heterogeneous base catalyst, namely, sodium silicate catalyst was placed into the reactor. The feed was soybean oil mixed with methanol (Acros, UN1230) in a 6:1 molar ratio. A charge of 300 cc was used. The operating temperature was 60° C. and the pressure was 50 psig above autogeneous conditions. The velocity ranged from 0.26 and 0.31 m/s. 10 watts of microwave power (1 W/cc) was applied to the catalyst bed as the feed/product mixture flowed. After 30 minutes a sample was collected and centrifuged. The top layer was then analyzed using the GC.

Figure 8:
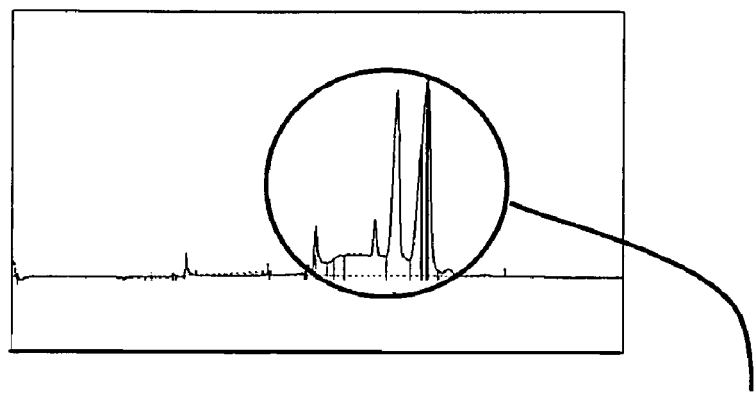
FIG. 8 shows GC plots of feed soybean oil and the microwave process biodiesel.
Figure 8:
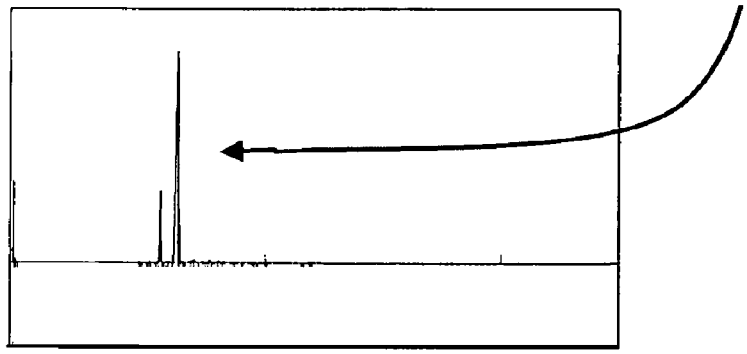

FIG. 8 presents the GC plots of the feed soybean oil and the microwave process product, which is biodiesel. The GC indicated 100% conversion of the soybean oil triglycerides.

Example 3

Effect of High Feed Velocity and Heterogeneous Catalyst on Heterogeneous Transesterification Using the CSB system illustrated in FIG. 7, 10 cc of heterogeneous base catalyst (sodium silicate) was placed into the reactor. A 4:1 (molar) methanol to soybean oil (SBO) mixture feed was used. The operating temperature was 80° C.

Figure 9:
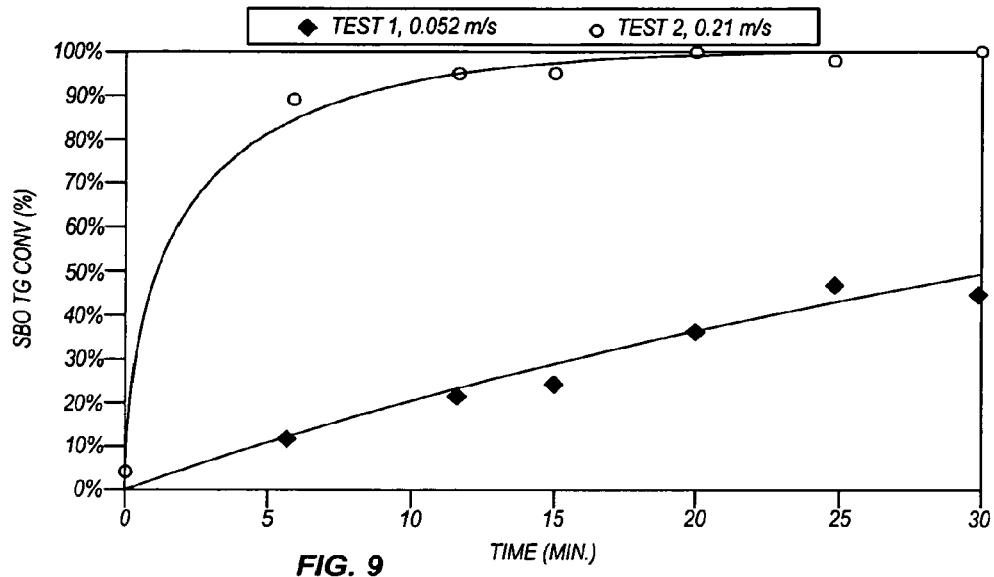
FIG. 9 shows a chart of an effect of velocity using a heterogeneous base catalyst.

FIG. 9 shows the TG conversion as a function of time. The graph shows that as the velocity increased from 0.052 m/s (Test 1) to 0.208 m/s (Test 2), the rate of conversion increased. The TG conversion more than doubled from 45% at 0.052 m/s to 100% at 0.208 m/s at 30 minutes or a LHSV of 60. This data also demonstrates that, contrary to the prior art; lower methanol to SBO ratios can be used to obtain 100% conversion with a heterogeneous base catalyst.

Example 4

Effect of Microwave Energy used with Heterogeneous Catalyst and Intermediate Velocity Flow Conditions on Transesterification Using the CSB system illustrated in FIG. 7, 10 cc of heterogeneous base catalyst (sodium silicate) was placed in the reactor. For both tests, the feed was a 6:1 (molar) methanol to SBO mixture; the operating temperature was 60° C.; and the feed velocity was 0.104 m/s.

Figure 10:
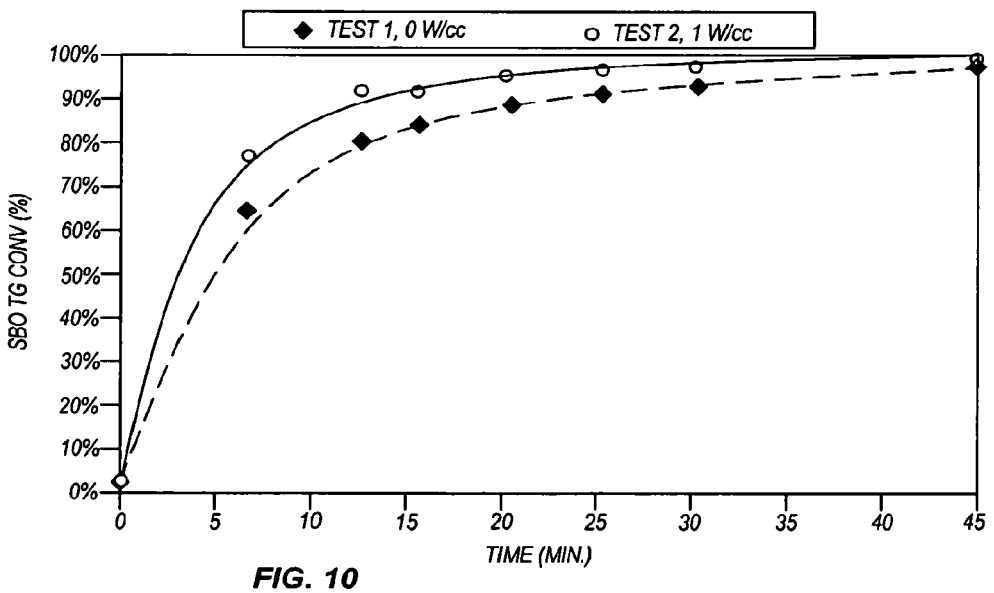
FIG. 10 shows a chart of a microwave effect with heterogeneous base catalyst at 0.104 m/s and a 6:1 (molar) methanol to SBO feed rate.

FIG. 10 shows the TG conversion as a function of time. The graph shows that when 10 watts of microwave power was applied (1 W/cc), the reaction rate improved. Using a LHSV of 45, 100% conversion was obtained with a heterogeneous base catalyst, an intermediate velocity, and small amounts of microwave energy applied compared to 98% without microwaves. This amounts to a 25% reduction in process time to achieve 100% conversion.

Example 5

Effect of Microwave Energy used with Heterogeneous Base Catalyst and Low Velocity Flow Conditions on Transesterification Using the CSB system illustrated in FIG. 7, 10 cc of heterogeneous catalyst (sodium silicate) was placed in the reactor, and two tests were performed. For both tests, the feed was a 4:1 (molar) methanol to SBO mixture; the operating temperature was 80° C.; and the flow rate was 0.0508 m/s.

Figure 11:
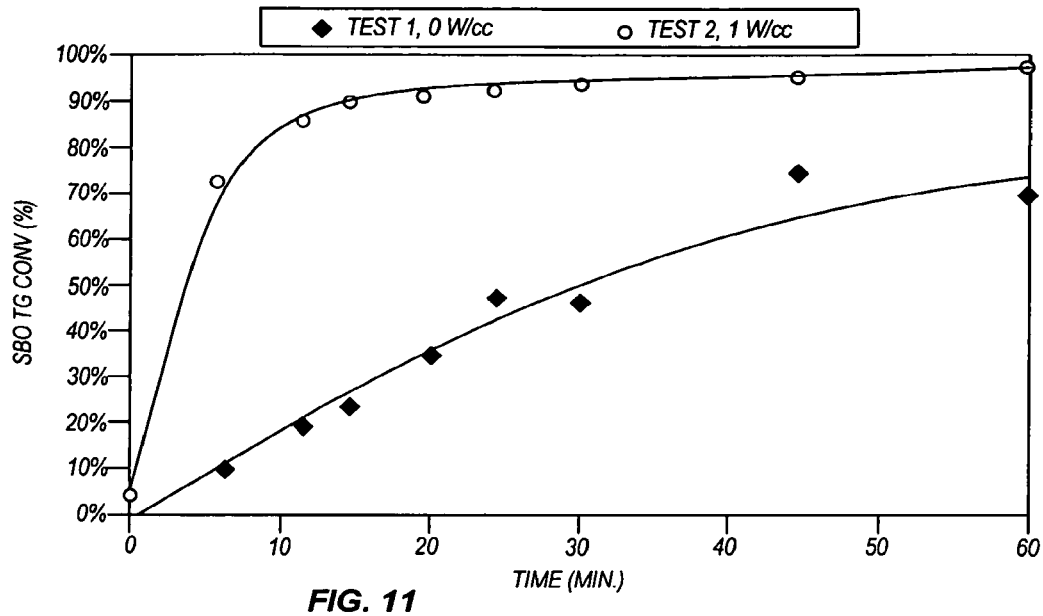
FIG. 11 shows a chart of a microwave effect with heterogeneous base catalyst at 0.052 m/s and a 4:1 (molar) methanol to SBO feed rate.

FIG. 11 shows the TG conversion as a function of time. The graph shows that when 10 watts of MW power was applied (1 W/cc), the conversion efficiency improved. At 60 minutes (LHSV of 30), 97% conversion was obtained with a heterogeneous base catalyst, a low velocity flow, and small amounts of microwave energy applied compared to less than 70% without microwaves. This amounts to halving the process time to high conversation.

Example 6

Effect of Feed Velocity and Oil-Alcohol Ratio using a Heterogeneous Catalyst Using the CSB system illustrated in FIG. 7, 10 cc of heterogeneous base catalyst (sodium silicate) was placed in the reactor. For all tests, the operating temperature was 80° C. Microwave energy was not used.

Table 6.1 shows the TG conversion as a function of time and LHSV. The first two tests compare two flow rates using a 4:1 (molar) methanol to SBO feed mixture. The last two tests compare the same two flow rates using a 6:1 (molar) methanol to SBO feed mixture. Several conclusions can be drawn from this data. The higher methanol to SBO ratio provides faster conversion for both velocity settings, 0.052 m/s and 0.208 m/s. Higher velocities allow for the use of lower methanol to SBO ratios, which provides for higher throughput and lower production costs.

TABLE 6.1

Comparisons of Feed Conversion based on Alcohol to Oil Ratios and Feed Velocity at 80° C. without microwaves

| Time | | 4:1 | | 6:1 | |
|---|---|---|---|---|---|
| (min.) | LHSV | 0.052 m/s | 0.208 m/s | 0.052 m/s | 0.208 m/s |
| 12 | 150 | 20.7% | 95.0% | 95.8% | 99.3% |
| 15 | 120 | 23.2% | 95.3% | 97.9% | 99.6% |
| 20 | 90 | 35.2% | 100.0% | 99.1% | 100.0% |
| 25 | 72 | 46.9% | 98.5% | 99.9% | 100.0% |
| 30 | 60 | 44.9% | 100.0% | 100.0% | 100.0% |

Example 7

Effect of Temperature on Heterogeneous Catalyst and Feed Velocity

Using the CSB system shown in FIG. 7, 10 cc of sodium silicate catalyst was placed in the reactor. For both tests, the feed was a 6:1 (molar) methanol to SBO mixture and a flow rate of 0.156 m/s.

Figure 12:
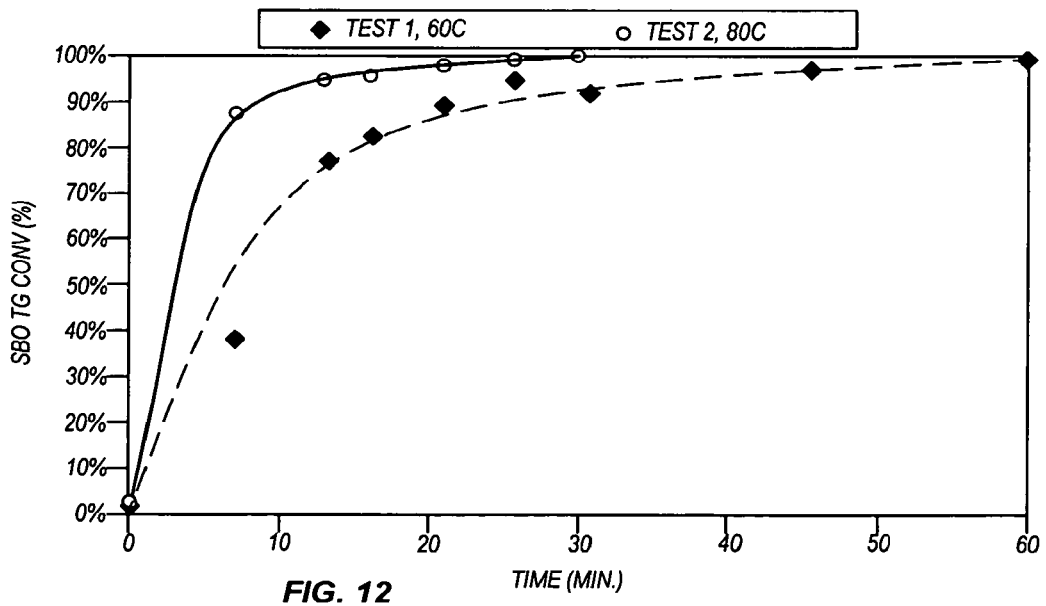
FIG. 12 shows a chart of a temperature effect with heterogeneous base catalyst at 0.156 m/s.

FIG. 12 shows the TG conversion as a function of time. One test was run at 60° C. and the other at 80° C. The graph shows that the process rate increased approximately 33% as the temperature increased from 60° C. to 80° C. This indicates that higher temperature promotes higher reaction rates.

Figure 13:
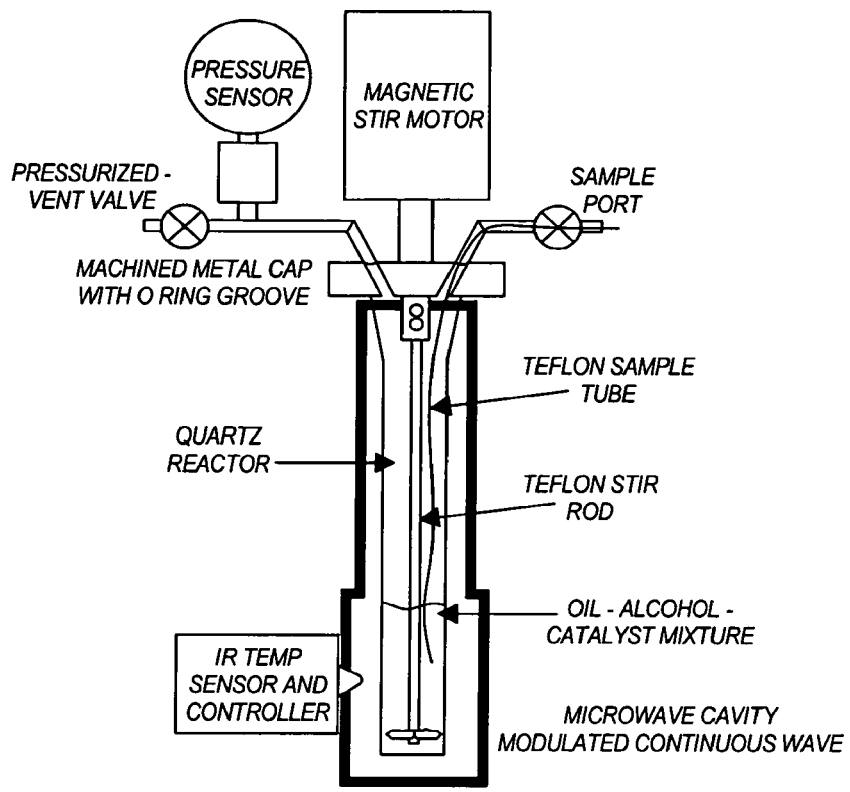
FIG. 13 is a batch, microwave enhanced transesterification/esterification reactor embodying the invention.

Experimental Set-up for Microwave Enhanced Batch Esterification and Transesterification Tests Batch tests, as shown in FIG. 13, were conducted using a modified 600 watt, 2.45 GHz, CEM Corporation Star microwave system. The control allowed for the setting of microwave power duty cycle from 1 to 100%. A custom reactor was designed of quartz and stainless steel. The steel top of the reactor was fitted with three ports. The center port was a feed-through for a stir rod. The second and third ports allow for gas pressurization, venting and sampling.

The initial tests were conducted at or near atmospheric pressure. A magnetic high-pressure stirrer (Pressure Products, Inc., Mixer M11-006) was added to the batch system to allow elevated pressure testing along with a sampling port. A Teflon® by Dupont stirrer was employed to mix the oil/alcohol/catalyst mixture. A mass balance was performed for each test.

A weighed amount of plant oil or animal fat or rendered oil was added to the open quartz tube. This was followed by weighed amounts of heterogeneous catalyst and methanol. If a liquid or dissolved catalyst was used, it was first premixed with alcohol. The catalyst-alcohol pre-mix was then added to the oil-feed.

Once the reactants, ranging in volume from 50-100 cc, were placed in the quartz tube, a Buna N or Viton O-ring and the stainless steel reactor lid were positioned and tightened in place. The microwave power duty cycle for heating the mixture to operating temperature was set at 50% or 3-4 W/cc. That is, the microwave operated at 50% power.

The rpm setting of the mix motor and Teflon stirrer affect many variables including reactant mixing, heterogeneous catalyst powder suspension, the reactant and product shear at the catalyst interface, and temperature uniformity. Tests indicated that setting the magnetic stirrer to yield approximately 750 rpm provided a good balance among the above variables and allowed for the novel results of a variety of heterogeneous and homogeneous catalysts.

The stir motor was set to yield approximately 750 rpm and reactants were allowed to mix for one minute for the batch tests conducted in the following examples.

The temperature set point was set to the desired operating temperature. Time zero was the time the microwave power was started. When the reactant temperature reached the desired temperature set point, usually after 2-3 minutes, the microwave duty cycle was reduced to 10-20% or 0.6-0.8 W/cc to maintain the process temperature. That is, the microwave operated at 10-20% power and was turned on and off in order to maintain the desired temperature of the process.

Example 8

Microwave Enhanced Heterogeneous Base Catalyzed Transesterification—Effect of Water Added to Methanol The following is an example of accelerated conversion using microwaves, high shear, and the heterogeneous base catalyst (calcium hydroxide). Three tests were performed where the level of water added to anhydrous methanol was increased to determine the effect on TG conversion.

All the tests in this example were conducted with a 6:1 methanol to SBO molar ratio, and an operating pressure 50 psig above autogeneous, using the batch system shown in FIG. 8.1. The magnetic stirrer was set to yield approximately 750 rpm.

For each test the microwave setting for starting the test was 600 watts, 50% power duty cycle or 3-4 W/cc. When the reactant temperature reached the desired temperature set point of 100° C. (about 2 to 3 minutes), the microwave power duty cycle was reduced to 10% or 0.6 W/cc to maintain the process temperature. Each test was conducted for 60 minutes.

2 wt % calcium hydroxide heterogeneous base catalyst (Aldrich, 1305-62-0) was used for all three tests. Water added to anhydrous methanol yield the following concentrations: 0 wt %, 1 wt % and 5 wt %.

Figure 14:
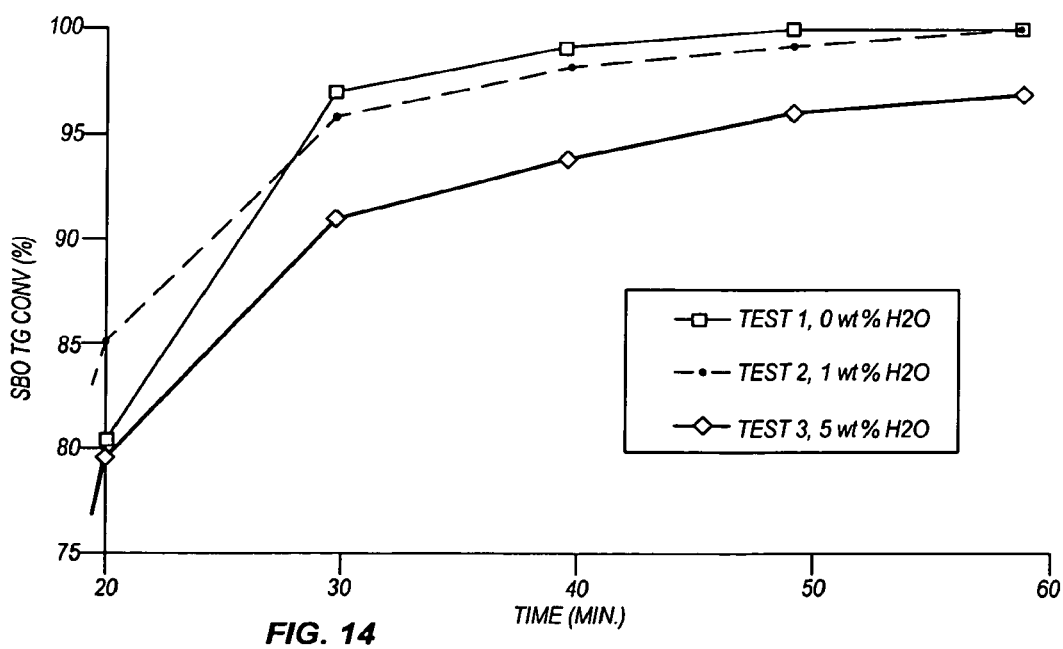
FIG. 14 shows a chart of an effect of water in methanol on heterogeneous base catalyst SBO TG conversion as a function of time.

The test results are plotted in FIG. 14. The results show that for Tests 1 and 2, 100% of the TGs were converted in 60 minutes (LHSV of 50). For Test 3, where 5 wt % water was added to methanol the level of TG conversion was reduced to 97%. This indicates that the water concentration in methanol, between 1 and 5 wt %, is sufficient to inhibit the TG conversion. These results also indicate that anhydrous methanol is not required for high levels of TG conversion, which will lower production costs.

Example 9

Effect of Alcohol to Oil ratio in the Microwave Enhanced Heterogeneous Base Catalyzed Transesterification of Castor Oil

Castor oil was transesterified with microwaves and a heterogeneous base catalyst using the batch system as shown FIG. 13. Two tests were performed showing the positive effect of higher alcohol to oil ratio on TG conversion process rates.

For both tests, 1.5 wt % hydrated sodium silicate powder was used. The operating temperature and process time were 120° C. and 10 minutes, respectively. The operating pressure was 50 psig above autogeneous and the magnetic stirrer was set to yield approximately 750 rpm.

The initial microwave power settings were 600 watts with a 50% power duty cycle, or 4 W/cc. When the reactant temperature reached the desired temperature set point of 120° C. (about 2 to 3 minutes), the microwave power duty cycle was reduced to 15% or 0.7 W/cc to maintain the process temperature.

Figure 15:
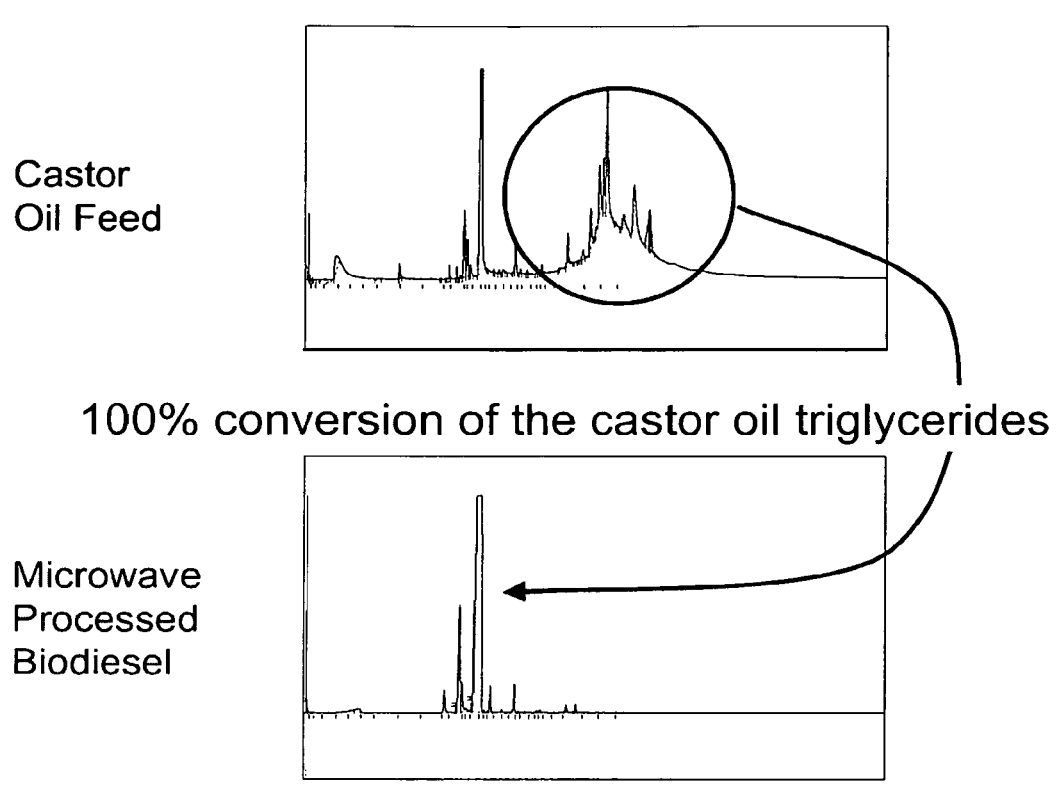
FIG. 15 shows GC plots of feed castor oil and the microwave process biodiesel.

For the first test, the methanol to castor oil molar ratio was 19:1. For the second test it was 6:1. The results of the first test show 100% conversion of the TG, FIG. 15, in 10 minutes (WHLV of 400). The results of the second test with a methanol to castor oil ratio of 6:1 show that 71% of the TGs were converted in 10 minutes. These results show that higher alcohol to oil ratios have a positive effect on TG conversion rates.

Example 10

Microwave Enhanced Near Ambient Pressure Homogeneous Acid Transesterification of SBO

Initial transesterification tests were run with a homogeneous acid catalyst using the batch system, shown in FIG. 13, without sampling ports or magnetically sealed stirrer. The test procedures were the same as the much-referenced Freedman tests with the exception of addition of microwave energy (0.6 W/cc). See Freedman, JAOS, Vol 61, October 84, which is hereby fully incorporated by reference. The reaction temperatures were at or near the boiling point of the alcohol (about 65° C.) selected for the test keeping the autogeneous pressure near ambient conditions.

In the first set of tests, the methanol to SBO molar ratio was 30:1 and the homogeneous acid catalyst was sulfuric acid (Fisher, A300-212). 1 wt % sulfuric acid based on SBO was added first to the methanol and allowed to mix. This methanol with sulfuric acid was then added to the SBO. The mixture was stirred at approximately 750 rpm, at 62° C., for 2 hours (WHSV=50).

The initial microwave power settings were 600 watts with a 10% power duty cycle, or about 1 W/cc. When the reactant temperature reached the desired temperature set point of 62° C., 2 to 3 minutes, the microwave power cycled to maintain the process temperature (about 0.3 W/cc).

The microwave enhanced process provided a four-fold increase in TG conversion of over 8% compared to less than 2% for the prior art without microwaves.

In the second set of tests, butanol was used instead of methanol. The butanol to SBO molar ratio was 30:1 and the homogeneous acid catalyst was sulfuric acid. 1 wt % sulfuric acid based on SBO was added first to the methanol and allowed to mix. This methanol with sulfuric acid was then added to the SBO. The mixture was stirred at approximately 750 rpm, at 117° C., for 1 hour (WHSV=100).

The initial microwave power settings were 600 watts with a 10% power duty cycle, or about 1 W/cc. When the reactant temperature reached the desired temperature set point of 114° C. (about 9 minutes), the microwave power duty cycle was adjusted to 0.5 W/cc to maintain the process temperature.

The microwave enhanced process provided a 36% increase in TG conversion for over 92% conversion compared to less than 68% conversion for the prior art without microwaves (see Freedman, JAOS, Vol 61, October 84).

Example 11

Microwave Enhanced Homogeneous Acid Transesterification at Elevated Temperature and Pressure using Methanol

The following is an example of accelerated conversion using microwaves at higher temperature and pressure and lower alcohol to oil ratio. The batch system had a sampling port attached and a sealed magnetic stirrer as shown in FIG. 13. Samples were collected and analyzed as plotted in FIG. 16.

The test was conducted with a 30:1 methanol to SBO molar ratio and the homogeneous acid catalyst was sulfuric acid. 1 wt % sulfuric acid based on SBO was added first to the methanol and allowed to mix. This methanol with sulfuric acid was then added to the SBO. The mixture was stirred at approximately 750 rpm and the operating pressure was set to 50 psig above autogeneous. The initial microwave power settings were 600 watts with a 10% power duty cycle, or about 1 W/cc. When the reactant temperature reached the desired temperature set point of 120° C., about 14 minutes, the microwave duty cycle was adjusted to 0.5 W/cc to maintain the process temperature.

Figure 16:
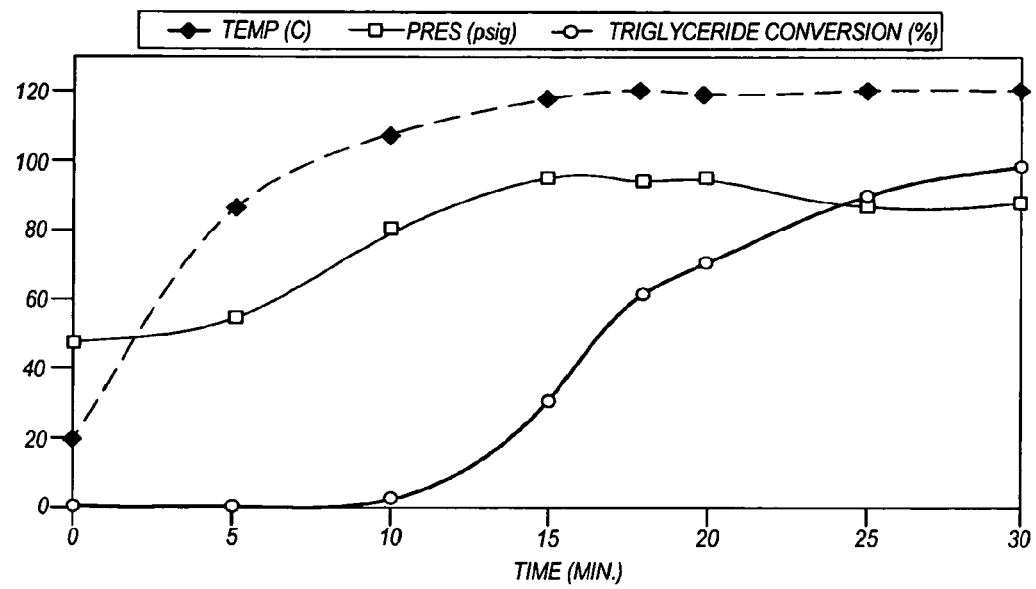
FIG. 16 shows a chart of a microwave enhanced homogeneous acid transesterification of SBO.

FIG. 16 shows that 14 minutes after reaching operating temperature (WHSV=400), the TG conversion was over 97%.

Example 12

Microwave Enhanced Homogeneous Acid Test at Elevated Temperature and Pressure using Butanol and a Lower Butanol to Soybean Oil Ratio

Figure 17:
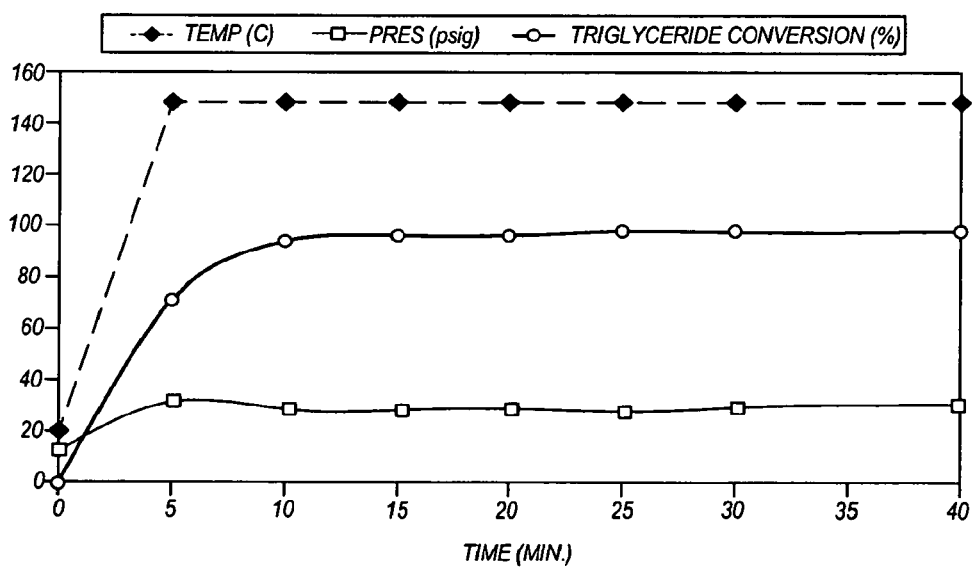
FIG. 17 shows another chart of a microwave enhanced homogeneous acid transesterification of SBO.

This test was performed using the batch system with sampling port attached as shown in FIG. 13. This test demonstrated accelerated conversion using microwaves at higher temperature and pressure and with a lower alcohol to oil molar ratio, as shown in FIG. 17. The test was conducted with a 6:1 butanol to SBO molar ratio, 1 wt % sulfuric acid, and an operating pressure 15 psig above autogeneous.

The initial microwave power settings were 600 watts with a 50% power duty cycle, or about 5 W/cc. When the reactant temperature reached the desired temperature set point of 150° C., 2 to 3 minutes, the microwave power duty cycle was reduced to 10% or 1 W/cc to maintain the process temperature.

At 10 minutes (WHSV=600), the TG conversion was 90% and at 30 minutes it was over 99% (WHSV=200).

Example 13

Heterogeneous Acid Catalyst Conversion Results for a Mixed Feed

The heterogeneous acid catalyst can be used for either esterification or transesterification. The following is an example of accelerated conversion of a mixed feed containing 20 wt % stearic acid (FFA) in soybean oil (TG) using the microwave batch system.

All four tests in this example were conducted with a 6:1 methanol to SBO molar ratio, and an operating pressure 50 psig above autogeneous, using the batch system shown in FIG. 13. The magnetic stirrer was set to yield approximately 750 rpm.

For each test the microwave setting for starting the test was 600 watts, 50% power duty cycle or 3-4 W/cc. When the reactant temperature reached the desired temperature set point of 120° C. (about 2 to 3 minutes), the microwave power duty cycle was reduced to 10% or 0.6 W/cc to maintain the process temperature. Each test was conducted for 60 minutes.

Table 13.1 shows the results for four catalysts. The first test uses a homogeneous catalyst, 1 wt % sulfuric acid. The conversion level of 98% of the FFA and 36% of the TG at one hour is far faster than what is reported in the literature (Canakci, M., Gerpin, J, Paper No. 016049, 2001 ASAE Annual International Meeting, Sacramento, Calif., Jul. 30-Aug. 1, 2001).

The next three tests used two types of heterogeneous acid catalysts, namely, iron sulfate ($Fe_2(SO_4)_3$) powder (Alfa Aesar, 33316), zeolite ZSM-5 powder (Zeolyst International), and iron sulfate coated on ZSM-5 powder at a 10 wt % level.

The iron sulfate heterogeneous acidic catalyst demonstrated conversions of TGs, 56%, and FFAs, 98%, comparable to the dissolved liquid acid, although using a higher catalyst weight percent. The ZSM-5 powder demonstrated high conversion of the FFAs, 93%, but not the TG, 0%, indicating it is a weaker acid than iron sulfate.

ZSM-5 is a zeolite that is more easily formed into a high surface area pellet or extrudate than is iron sulfate. As such, an iron sulfate coated ZSM-5 powder would be more readily scaled for use in a commercial reactor. The 10% iron sulfate coated ZSM-5 showed improved conversion over the ZSM-5 material alone with a TG conversion of 13%, and a FFA conversion of 95%.

TABLE 13.1

Homogeneous and Heterogeneous Acid Catalyst Conversion Results for a Mixed Feed

| Catalyst | wt % | TG % Converted | FFA (StA) % Converted |
| --- | --- | --- | --- |
| Dissolved $H_2SO_4$ | 1% | 35.9% | 98.1% |
| $Fe_2(SO_4)_3$ powder | 5% | 55.9% | 98.3% |
| ZSM-5 powder | 5% | 0.0% | 92.6% |
| $Fe_2(SO_4)_3$-ZSM-5 coated powder | 5% | 13.0% | 95.1% |

Example 14

Two-Step Microwave Enhanced Heterogeneous Catalyst Conversion of Mixed Feed

The following is an example of two-step conversion of mixed feed using microwaves and heterogeneous acid and base catalysts, using the batch system as shown FIG. 13. The mixed feed was a mixture of 20 wt % oleic acid (FFA) in soybean oil (TG). Oleic acid is another free fatty acid seen in animal and plant oils.

For the first step, heterogeneous acid catalysis was used to convert the FFA to FAAE. The test was conducted with a 6:1 methanol to TG/FFA molar ratio. The heterogeneous acid catalyst used was an ion exchange resin purchased from Rohm and Haas, Amberlyst 35 dry. The concentration used was 3.66 wt %. The operating pressure was 50 psig above autogeneous and the magnetic stirrer was set at approximately 750 rpm.

The initial microwave power settings were 600 watts with a 50% power duty cycle, or 4 W/cc. When the reactant temperature reached the desired temperature set point of 120° C., 2 to 3 minutes, the microwave power duty cycle was reduced to 10% or 0.6 W/cc to maintain the process temperature. By 30 minutes, 100% of the FFAs were converted. This would yield a WHSV of 55. It is estimated that the TG conversion after the first step was about 20%.

The product mixture was centrifuged and separated from the heterogeneous acid catalyst. The methanol and water were evaporated in the MDS 2000 batch microwave by heating to 110° C. for 10 minutes. Fresh methanol was then added to the first step product mixture to yield a 6:1 methanol to SBO molar ratio.

For the second step, heterogeneous base catalysis was used to convert the TG to FAAE. The heterogeneous base catalyst used was calcium hydroxide and the concentration used was 5 wt %. The operating pressure was 50 psig above autogeneous. The stirrer motor was set to yield approximately 750 rpm.

The initial microwave power settings were 600 watts with a 50% power duty cycle, or 4 W/cc. When the reactant temperature reached the desired temperature set point of 100° C., under 2 minutes, the microwave power duty cycle was reduced to 10% or 0.6 W/cc to maintain the process temperature. By 20 minutes, 100% of the TGs were converted. This would yield a WHSV of 60.

Example 15

One-Step Microwave Enhanced Heterogeneous Catalyst Conversion of Mixed Feed

The following is an example of accelerated conversion of mixed feed using microwaves and heterogeneous acid catalyst, iron sulfate, using the batch system as shown FIG. 13. The mixed feed was a mixture of 20 wt % oleic acid (FFA) in soybean oil (TG). The test was conducted with a 6:1 methanol to TG/FFA molar ratio. The operating pressure was 10 psig above autogeneous. 5 wt % of iron sulfate powder was tested for its effectiveness to convert both the mixed feed's FFAs and TGs. The stir motor was set to yield approximately 750 rpm.

The initial microwave power settings were 600 watts with a 50% power duty cycle, or 4 W/cc. When the reactant temperature reached the desired temperature set point of 130° C., 3 to 4 minutes, the microwave power duty cycle was reduced to 10% or 0.6 W/cc to maintain the process temperature.

A sample collected after 1 hour was centrifuged and analyzed with a GC. The results indicated that 100% of the oleic acid was converted as was over 96% of the TG.

Example 16

One-Step Microwave Enhanced Homogeneous Catalyst Conversion of Yellow Grease

Yellow grease is a rendered product of mixed animal and plant oils. The sample evaluated had an 18% FFA content as shown FIG. 18.

The yellow grease sample was processed with microwaves and a homogeneous acid catalyst, using the batch system as shown FIG. 13.

For this test, the 2.0 wt % sulfuric acid was used. The operating temperature and process time were 120° C. and 60 minutes respectively. The operating pressure was 50 psig above autogeneous and the magnetic stirrer was set to yield approximately 750 rpm. The methanol to yellow grease (TG/FFA) molar ratio based on 18% FFA was 9:1.

The initial microwave power settings were 600 watts with a 50% power duty cycle, or 4 W/cc. When the reactant temperature reached the desired temperature set point of 120° C., 2 to 3 minutes, the microwave power duty cycle was reduced to 15% or 0.7 W/cc to maintain the process temperature.

Figure 18:
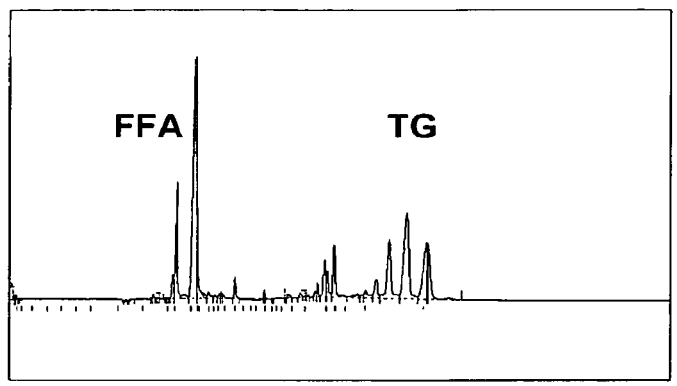
FIG. 18 shows GC plots of mixed feed yellow grease and the microwave process biodiesel.
Figure 18:
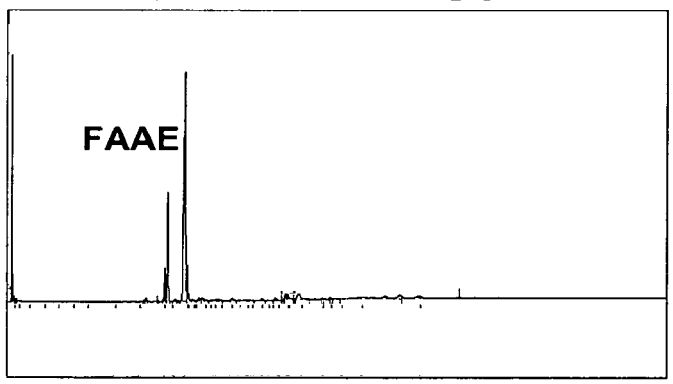
Figure 19:
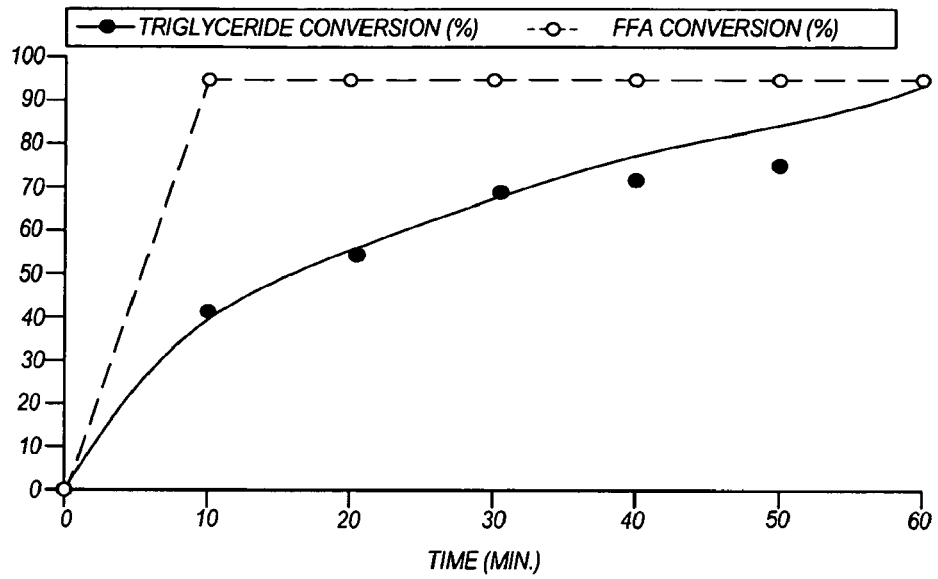
FIG. 19 shows a chart of a FFA and TG conversion as a function of time.

FIG. 19 plots the FFA and TG conversion as a function of time showing that the FFA are almost entirely converted by the time the first sample is collected, 10 minutes. The test results in FIG. 18 show that over 99% of the FFAs were converted and 98% of the TGs were converted in one hour (WHSV of 50). This result shows over a 10 fold improvement in processes rates compared to conventional homogeneous catalytic processing of mixed feed (Canakci, M., Gerpin, J, Paper No. 016049, 2001 ASAE Annual International Meeting, Sacramento, Calif., Jul. 30-Aug. 1, 2001).

Example 17

Microwave Enhanced Homogeneous and Heterogeneous Acid Esterification of Crude Tall Oil Free Fatty Acids Tall oil (or tallol) is a by-product of the paper pulp industry, obtained by acid treatment of the alkaline liquors from the digestion of pine wood. The composition may vary considerably, but a typical mixture would contain 35-40% rosin acids, 50-60% fatty acids, and 5-10% unsaponifiable materials.

The sample evaluated had an acid number of 145 indicating a percent FFA and percent rosin acids total of 76%.

Two tests were performed with the Crude Tall Oil sample using the microwave batch system shown FIG. 13. The first test was with a homogeneous acid catalyst, 2 wt % sulfuric acid, and the second was with a heterogeneous acid catalyst, 5 wt % acid resin beads (Amberlyst 35 dry from Rohm and Haas).

The following test conditions were used for both tests. The operating temperature was 120° C., the operating pressure was 50 psig above autogeneous and the magnetic stirrer was set to yield approximately 750 rpm. For both tests the methanol to crude tall oil molar ratio was 6:1.

The initial microwave power settings were 600 watts with a 50% power duty cycle, or 4 W/cc. When the reactant temperature reached the desired temperature set point of 120° C., 2 to 3 minutes, the microwave power duty cycle was reduced to 15% or 0.7 W/cc to maintain the process temperature.

The samples were collected, centrifuged and analyzed using gas chromatography. The GC column available at the time of the test could not distinguish between FFA and rosin acid content. However, the GC did show that a 45% reduction in the FFA/rosin acid content occurred with the sulfuric acid catalyst at 10 minutes (WHSV of 300) and with the acid resin beads in 40 minutes (WHSV of 30). This data was corroborated with acid number analysis. Thus under similar processing conditions homogeneous reaction is 10 times faster than the heterogeneous reaction. In practice one would need to determine if this faster reaction rate offsets the cost of catalyst consumption, neutralization and removal.

Example 18

Microwave Enhanced Homogeneous Acid Esterification of Highly Acidulated Soapstock Soapstock is a by-product of the caustic refining of vegetable oils. The major components are sodium salts of fatty acids, mono-, di- and tri-glycerides with up to 50% water. Treatment with sulfuric acid precipitates the organics, allowing water separation. This acidulated soapstock, sometimes called acid oil, contains up to 90% total fatty acids and 50% free fatty acids.

The highly acidulated soapstock sample evaluated had an acid number of 145 indicating a free fatty acid content of 96%.

Two tests were performed with the highly acidulated soapstock sample using the microwave batch system shown FIG. 13. The first test was with a homogeneous acid catalyst, 2 wt % sulfuric acid, and the second test used 0.1 wt % sulfuric acid.

The following test conditions were used for both tests. The operating temperature was 120° C., the operating pressure was 50 psig above autogeneous and the magnetic stir was set to yield approximately 750 rpm. For both tests the methanol to highly acidulated soapstock molar ratio was 6:1.

The initial microwave power settings were 600 watts with a 50% power duty cycle, or 4 W/cc. When the reactant temperature reached the desired temperature set point of 120° C., 2 to 3 minutes, the microwave power duty cycle was reduced to 15% or 0.7 W/cc to maintain the process temperature.

The samples were collected, centrifuged and analyzed using gas chromatography.

The GC test results showed that a 100% reduction in the FFA acid content occurred with the 2 wt % sulfuric acid catalyst at 10 minutes (WHSV of 300) and with the 0.1 wt % sulfuric acid catalyst in 40 minutes (WHSV of 1500). The lower acid content had an effective 5 times greater processing rate but took four times as long to achieve complete FFA conversion. In practice one would need to determine if this faster time to complete the reaction offsets the higher cost of catalyst consumption, neutralization and removal.

Example 19

Microwave Enhanced Homogeneous Acid Esterification for 100% Free Fatty Acid Feed For this sample, the CSB system shown in FIG. 7 was used to process 100% oleic acid feed. Sulfuric acid was the homogeneous acid catalyst tested. It was added to the methanol so that a concentration of 0.25 wt % sulfuric acid by the weight of the oleic acid (FFA) was obtained. The acidified methanol was added to FFA to obtain a 6:1 molar methanol to FFA ratio. The target operating temperature was 100° C. The fluid velocity was 0.208 m/s and the operating pressure was 20 psig above autogeneous.

Figure 20:
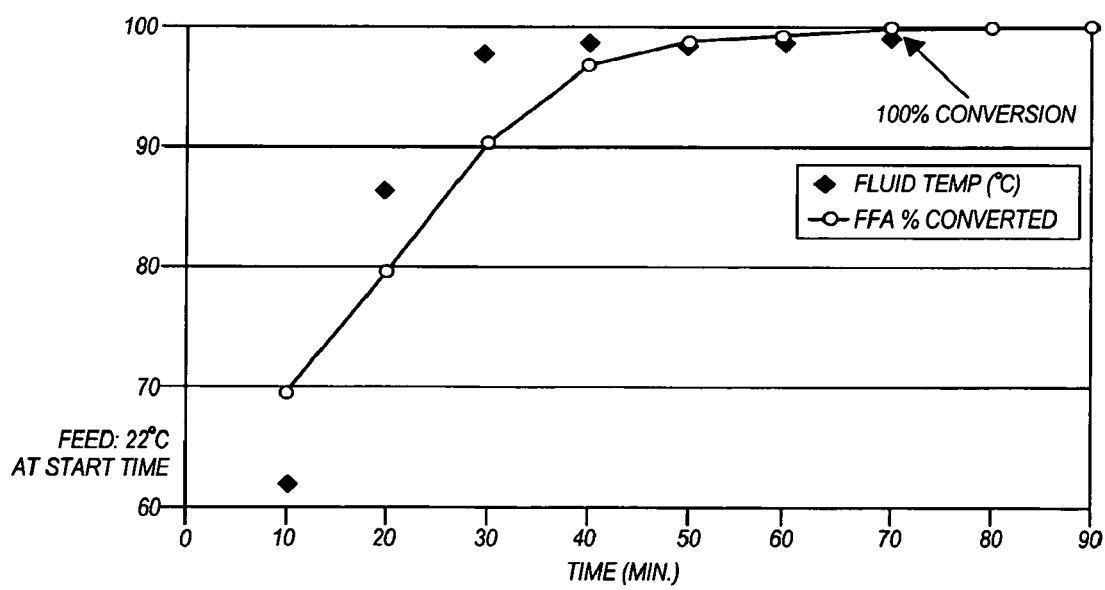
FIG. 20 shows a chart of a microwave enhanced homogeneous acid esterification of 100% Oleic Acid (FFA) as a function of time.

One major change was implemented to the test procedures using heterogeneous catalysts, presented in Example 2. Instead of sending the feed through the by-pass loop to preheat, the feed was sent immediately through the flow through microwave reactor. Thus at time zero, the feed with homogeneous catalyst was at room temperature as indicated in FIG. 20.

Also at time zero, 20 watts of microwave power (2 W/cc) were applied to the flow through microwave reactor (without heterogeneous catalyst) as the feed/product mixture flowed.

Samples were collected every ten minutes and the fluid temperature was recorded. The samples were centrifuged and analyzed using the gas chromatograph. FIG. 20 is a plot of the FFA conversion and fluid temperature with time. Within 70 minutes of the start of the test and after 40 minutes at operating temperature of 100° C., 100% of the oleic acid was converted. This is a WHSV of over 340.

This example demonstrates that lower catalyst content and lower bulk operating temperature can be used with emulsification and microwaves.

Example 20

Transesterification with Combined Heterogeneous & Homogeneous Catalysis

The CSB system described in FIG. 7 was used to perform the following three tests using a homogeneous alkaline catalyst, heterogeneous alkaline catalyst, and the combination of the two, respectively. This series of tests shows the advantages of combining both heterogeneous and homogeneous catalysis.

Table 20.1 shows the tests conditions for the three tests. In all three tests, soybean oil (SBO) was mixed with methanol in a 6:1 molar ratio, the feed velocity is 0.208 m/s, the operating pressure was 50 psig above autogeneous conditions, and the operating temperature was 100° C.

For Test 1, the alkaline homogeneous catalyst was sodium hydroxide (NaOH), which was dissolved into methanol, to yield a concentration of 500 ppm (0.05 wt % with respect to SBO).

For Test 2, alkaline heterogeneous catalyst was an extrudate formed from a mixture of sodium silicate and aluminum hydroxide. The mixed ratio of the two ingredients by weight was 50-50. The mixture was extruded (1/16" diameter) and fired in air at 450° C. for three hours. 10 cc of catalyst was placed in the microwave flow-through reactor.

For Test 3, the same alkaline heterogeneous catalyst was re-used along with the addition of 500 ppm NaOH dissolved into the methanol prior to mixing with the SBO.

For all three tests microwave power levels of 20 W or 2 W/cc were used. However, in Test 1 the microwave mode was continuous wave versus pulsed mode for Tests 2 and 3. The test time for Test #1 was 90 minutes and 70 minutes (30 LHSV) for Tests 2 and 3.

For Tests 1 and 3, a different start up procedure was used compared to the test procedures using heterogeneous catalysts, presented in Example 2. Instead of sending the feed through the by-pass loop to pre-heat, the feed was sent immediately through the flow through microwave reactor. Thus at time zero, the feed was at room temperature.

The samples for all the tests were collected, centrifuged, and the liquid phases analyzed by GC. The results tabulated in Table 20.1 show that the TG conversion was 94%, 83%, and 100% for Tests 1, 2 and 3 respectively. This test data showed that for conditions where neither the homogeneous catalyst nor the heterogeneous catalyst succeeded to yield 100% TG conversion, the combination of the two did.

TABLE 20.1

Transesterification Test Conditions and Results using Homogeneous Alkaline catalyst, Heterogeneous Alkaline Catalyst, and the Combination of the Two

| Test Condition | Test 1 | Test 2 | Test 3 |
|---|---|---|---|
| Catalyst | 500 ppm NaOH | Sodium Silicate Extrudate | Sodium Silicate Extrudate plus 500 ppm NaOH |
| Feed | SBO | SBO | SBO |
| MeOH/SBO Molar Ratio | 6:1 | 6:1 | 6:1 |
| Pressure above autogeneous (psig) | 50 | 50 | 50 |
| Operating Temp (C.) | 100 | 100 | 100 |
| Microwave Setting | 20 W, CW | 20 W, Pulsed | 20 W, Pulsed |
| Velocity (m/s) | 0.208 | 0.208 | 0.208 |
| Test Time (min.) | 90 | 70 | 70 |
| SBO TG conversion (%) | 94% | 83% | 100% |

Example 21

Esterification with Combined Heterogeneous & Homogeneous Catalysis

The CSB system described in FIG. 7 was used to perform the following three tests using a homogeneous acid catalyst, heterogeneous acid catalyst, and the combination of the two, respectively. This series of tests shows the advantages of combining both heterogeneous and homogeneous catalysis.

Table 21.1 shows the tests conditions for the three tests. In all three tests the mixed feed velocity was 0.208 m/s, the operating pressure was 50 psig above autogeneous conditions, and the operating temperature was 100° C.

For Test 1, the acid homogeneous catalyst was sulfuric acid ($H_2SO_4$), which was dissolved into methanol, to yield a concentration of 1,000 ppm (0.1 wt % with respect to TG/FAA). For Test 2, the acid heterogeneous catalyst was an acid resin (Dowex DR-2030 from Dow Corning) of which 8 cc was placed in the microwave flow-through reactor. For Test 3, the same acid heterogeneous catalyst was re-used along with the addition of 1,000 ppm $H_2SO_4$ dissolved into the methanol prior to combining with the mixed feed.

The feed for Tests 1 and 3 was yellow grease with a free fatty acid content of 18 wt %. For test 2 the feed was soybean oil mixed with 20 wt % oleic acid. The test times for all three tests were similar, at 90 minutes for Test 1 and 87.5 minutes (30 LHSV) for Tests 2 and 3.

The three tests used similar microwave power levels of 20 W or 2 W/cc. However, in Test 1 the microwave mode was continuous wave versus pulsed mode for Tests 2 and 3.

For Tests 1 and 3, a different start up procedure was used compared to the test procedures using heterogeneous catalysts, presented in Example 2. Instead of sending the feed through the by-pass loop to pre-heat, the feed was sent immediately through the flow through microwave reactor. Thus at time zero, the feed was at room temperature.

The samples for all the tests were collected, centrifuged, and the liquid phases analyzed by GC. The results tabulated in Table 21.1 show that the FFA conversion was 35%, 55%, and 97% for Tests 1, 2 and 3 respectively. This test data showed that for conditions where the homogeneous catalyst and the heterogeneous catalyst yielded low FFA conversion, the combination of the two significantly improved performance by almost a factor of two.

TABLE 21.1

Esterification Test Conditions and Results using Homogeneous Acid catalyst, Heterogeneous Acid Catalyst, and the Combination of the Two

| Test Condition | Test 1 | Test 2 | Test 3 |
|---|---|---|---|
| Catalyst | 1,000 ppm H2SO4 | Acid Resin | Acid Resin plus 1,000 ppm H2SO4 |
| Feed | Yellow Grease with 18% FFA | SBO with 20% FFA | Yellow Grease with 18% FFA |
| MeOH to TG/FFA molar ratio | 6:1 | 6:1 | 6:1 |
| Pressure above autogeneous (psig) | 50 | 50 | 50 |
| Operating Temp (C.) | 100 | 100 | 100 |
| Microwave Setting | 20 W, CW | 20 W, Pulsed | 20 W, Pulsed |
| Velocity (m/s) | 0.208 | 0.208 | 0.208 |
| Test Time (min.) | 90 | 87.5 | 87.5 |
| FFA conversion (%) | 35% | 55% | 97% |

Example 22

Microwave and Emulsion for Homogeneous Base Transesterification

In his work Freedman (Freedman, JAOS, Vol 61, October 84) cites 98% TG conversion after 60 minutes of reaction at 60-63° C., ambient pressure, 0.5 wt % sodium methoxide catalyst, a 6:1 Methanol to SBO ratio. He states that traces of TG are always present because of equilibrium between products and reactants. Freedman used mechanical mixing and conventional heat.

For our test, we used 6:1 Methanol to SBO molar ratio, and the same temperature and pressure conditions. The same amount of catalyst, 0.5 wt %, was used, although the weaker sodium hydroxide base catalyst was substituted for sodium methoxide.

The two tests below show the effect of mixing, emulsions and microwaves on enhanced conversion.

The test set up used a 600 watt CEM MDS 2000 batch reactor with temperature and pressure feedback control. The procedures to obtain the test results were as follows. First 0.275 g of sodium hydroxide was dissolved 12 g of methanol. This mixture was added to 55 g of soybean oil. For test #1 mixture was placed in batch reactor, FIG. 13, to be mixed. The mixture was stirred to yield approximately 750 rpm, using the magnetic stirrer for 3 minutes. (Note: This is the standard stir setting for batch tests.) After being stirred for three minutes the mixture was poured into a Teflon vessel, sealed, and placed into the CEM batch reactor. The fiberoptic temperature sensor and pressure sensor were attached to the Teflon vessel. The microwave was set to operate at 600 watts, a power density for this feed volume of approximately 5 W/cc, with a temperature set point of 60° C., for 5 minutes. The feed heated to 60° C. in less than 15 seconds, and the microwave power duty cycle was estimated at 10%, 0.5 W/cc. The vessel was not equipped for mixing so no mechanical agitation was possible while the sample was processed using microwave energy.

The vessel was then cooled to 50° C. and the mixture was centrifuged for biodiesel and glycerol separation and analysis using gas chromatography.

The results of test #1 were 88% TG conversion in 5 minutes (WHSV of 2,400).

The same conditions were used for test #2 except that the mixture was placed in a high-speed mixer (approximately 22,000 rpm) for 3 minutes. This high speed mixing is sufficient to create a finer emulsion than that created with the magnetic stirrer. The results for Test #2 were 99.2% TG conversion in 5 minutes (WHSV of 2,400).

These results show that microwaves combined with emulsification yield a 12-fold increase in process rates when compared to Freedman's work. These results also show that finer emulsions provide for higher conversion levels and process rates prior to microwave processing.

Example 23

Microwave Enhanced Glycerol-Methyl Ester Separation

Biodiesel is typically produced from the transesterification reaction of triglycerides and methanol. This produces glycerol and a mixture of fatty acid methyl esters as products. These materials must be separated as the initial step in the preparation of commercial grade biodiesel fuel. Glycerol is the heavier material and tends naturally to sink to the bottom of the container, although this process can take several hours. The following experiment demonstrates the effectiveness of microwave treatment in reducing the separation time to minutes.

Glycerol and biodiesel were weighed directly into a blender. The two liquids were blended for 30 sec on low, 18,000 rpm and 30 sec on high, 22,000 rpm (total=60 sec) to produce an emulsion. Equal amounts of the emulsion were poured into three 100 ml glass centrifuge tubes (50 ml each). One tube was microwave treated at 65° C. for 10 min using the CEM microwave oven described in Example 22. The second tube was heated by conventional oven at 65° C. for 10 min. The third sample was kept at room temperature as a blank. All tubes were checked periodically for the separation of free glycerol.

Figure 21:
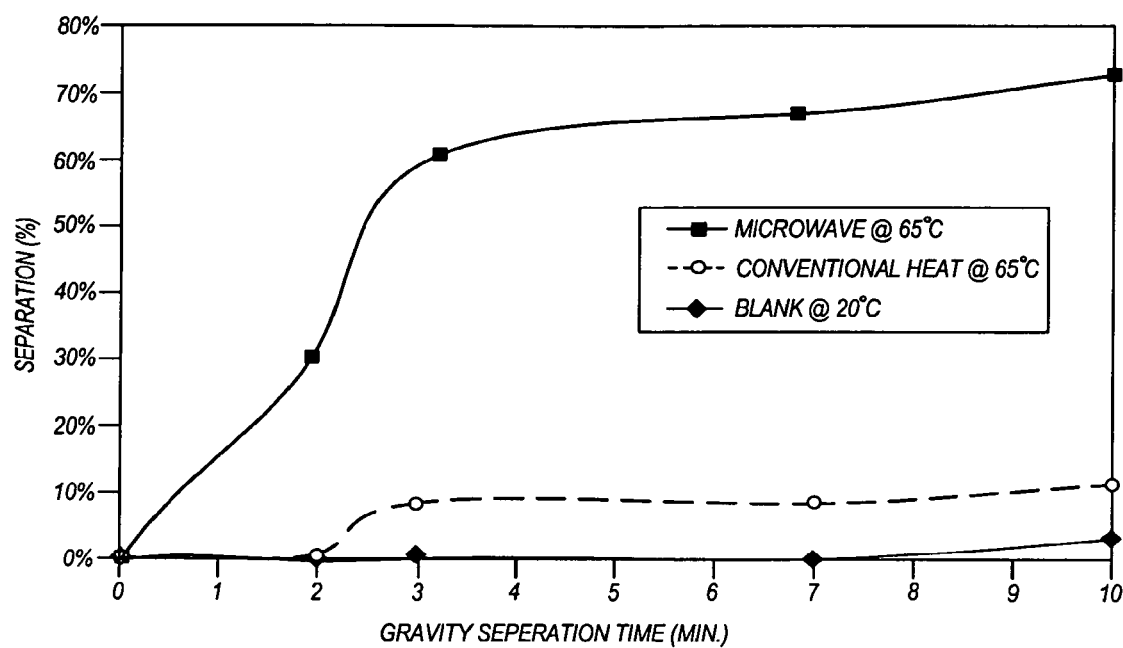
FIG. 21 shows a chart of a microwave enhanced glycerol-biodiesel separation.

The results are shown in FIG. 21. The Blank did not show separation until 10 min had passed. At 10 minutes a total of 3% of the glycerol had separated. The sample heated by conventional methods showed some separation after 3 minutes. After 10 min a total of 12% of the glycerol had separated. The sample heated by microwave energy showed separation after 2 min. After 10 min 75% of the glycerol had separated.

Prophetic Examples

Example 24

Feed Velocity—Heterogeneous Catalysis for Esterification and Transesterification In order to more clearly show the conversion enhancement provided by increasing flow velocity, the following tests could be performed. For comparison, certain variables are held relatively constant for each of the tests. The temperature would be held relatively constant for each test, such as at 60° C. or 80° C. The pressure would be held relatively constant for each test, such as at autogeneous. The alcohol to TG molar ratio would be held relatively constant for each test, such as at 4:1 or 6:1. The MW power would be held relatively constant for each test, such as at 0 W/cc or 1 W/cc. The amount and type of catalyst would be held relatively constant for each test, such as 10 cc of sodium silicate. The size and type of reactor set up would be held relatively constant for each test, such as the CSB system illustrated in FIG. 7. It should be understood that the precise test conditions could vary from those listed above, as long as the conditions are held relatively constant for the various tests being performed.

The test would involve measuring the time required to achieve 100% conversion for reactant flow velocities of about 0.001 m/s, 0.005 m/s, 0.01 m/s, 0.05 m/s, 0.10 m/s, 0.15 m/s, 0.20 m/s, 0.25 m/s, or any other desired flow velocity. Alternatively, the test could involve the measuring of the percent conversion at a given time period, such as 30 or 60 minutes, for each of the flow rates listed above. These tests would show how the reaction efficiency is affected by changing flow velocities.

In order to more clearly show the conversion enhancement provided by increasing flow velocity in combination with the effects of increased pressure, the above-described tests could be performed using a variety of pressure values. The test would involve measuring the time required to achieve 100% conversion using various combinations of flow velocity and pressure. Alternatively, the test could involve the measuring of the percent conversion at a given time period, such as 30 or 60 minutes, for various combinations of flow velocity and pressure. These tests would show how the reaction efficiency is affected by changing flow velocity and pressure. The proposed flow velocities are listed above, and the proposed pressures are autogeneous pressure, and 5 psig, 10 psig, 25 psig, 50 psig, and 100 psig above autogeneous pressure, or any other desired pressure.

In order to more clearly show the conversion enhancement provided by increasing flow velocity in combination with the effects of RF or MW energy, the above-described tests could be performed using a variety of RF or MW energy values. The test would involve measuring the time required to achieve 100% conversion using various combinations of flow velocity and MW energy. Alternatively, the test could involve the measuring of the percent conversion at a given time period, such as 30 or 60 minutes, for various combinations of flow velocity and MW energy. These tests would show how the reaction efficiency is affected by changing flow velocity and MW energy. The proposed flow velocities are listed above, and the proposed average MW power densities could be about 0.01 W/cc, 0.05 W/cc, 0.10 W/cc, 0.50 W/cc, 1 W/cc, 3 W/cc, 5 W/cc, 10 W/cc, 20 W/cc, 50 W/cc, 100 W/cc, or any other desired power density.

Example 25

Heterogeneous Catalyzed Esterification with Microwave Enhancement

In order to more clearly show the esterification enhancement provided by RF or MW radiation, the following tests could be performed. For comparison, certain variables are held relatively constant for each of the tests. The temperature would be held relatively constant for each test, such as at 60° C. or 80° C. The pressure would be held relatively constant for each test, such as at autogeneous. The alcohol to FFA molar ratio would be held relatively constant for each test, such as at 4:1 or 6:1. The flow velocity would be held relatively constant for each test, such as at 0.05 m/s or 0.10 m/s. The amount and type of catalyst would be held relatively constant for each test, such as 10 cc of an ion exchange resin. The size and type of reactor set up would be held relatively constant for each test, such as the CSB system illustrated in FIG. 7. It should be understood that the precise test conditions could vary from those listed above, as long as the conditions are held relatively constant for the various tests being performed.

The test would involve measuring the time required to achieve 100% conversion for MW-enhanced reactions using average MW power densities of about 0.01 W/cc, 0.05 W/cc, 0.10 W/cc, 0.50 W/cc, 1 W/cc, 3 W/cc, 5 W/cc, 10 W/cc, 20 W/cc, 50 W/cc, 100 W/cc, or any other desired power density. Alternatively, the test could involve the measuring of the percent conversion at a given time period, such as 30 or 60 minutes, for each of the power densities listed above. These tests would show how the reaction efficiency is affected by changing MW power densities.

In order to more clearly show the conversion enhancement provided by RF or MW energy in combination with the effects of increased pressure, the above-described tests could be performed using a variety of pressure values. The test would involve measuring the time required to achieve 100% conversion using various combinations of MW power density and pressure. Alternatively, the test could involve the measuring of the percent conversion at a given time period, such as 30 or 60 minutes, for various combinations of MW power density and pressure. These tests would show how the reaction efficiency is affected by changing MW power density and pressure. The proposed MW power densities are listed above, and the proposed pressures are autogeneous pressure, and 5 psig, 10 psig, 25 psig, 50 psig, and 100 psig above autogeneous pressure, or any other desired pressure.

In order to more clearly show the conversion enhancement provided by RF or MW energy in combination with the effects of high flow velocity, the above-described tests could be performed using a variety of flow velocities. The test would involve measuring the time required to achieve 100% conversion using various combinations of MW power density and flow velocity. Alternatively, the test could involve the measuring of the percent conversion at a given time period, such as 30 or 60 minutes, for various combinations of MW power density and flow velocity. These tests would show how the reaction efficiency is affected by changing MW power density and flow velocity. The proposed MW power densities are listed above, and the flow velocities are about 0.001 m/s, 0.005 m/s, 0.01 m/s, 0.05 m/s, 0.10 m/s, 0.15 m/s, 0.20 m/s, 0.25 m/s, or any other desired flow velocity.

Example 26

Emulsion Plus Microwave Enhancement—Homogeneous Catalysis for Esterification and Transesterification In order to clearly show the combined effect of emulsion and MW on the transesterification process, the following tests could be performed. For comparison, certain variables are held relatively constant for each of the tests. The temperature would be held relatively constant for each test, such as at 60° C. or 80° C. The pressure would be held relatively constant for each test, such as at autogeneous. The alcohol to TG molar ratio would be held relatively constant for each test, such as at 4:1 or 6:1. The flow velocity would be held relatively constant for each test, such as at 0.05 m/s or 0.10 m/s. The amount and type of catalyst would be held relatively constant for each test, such as 0.5% sodium hydroxide. The size and type of reactor set up would be held relatively constant for each test, such as the batch reactor illustrated in FIG. 13. It should be understood that the precise test conditions could vary from those listed above, as long as the conditions are held relatively constant for the various tests being performed.

The test would involve measuring the time required to achieve 100% conversion for transesterification reactions using various combinations of emulsion levels and MW power densities. Alternatively, the test could involve the measuring of the percent conversion at a given time period, such as 30 or 60 minutes, for various combinations of emulsion levels and MW power densities. These tests would show how the reaction efficiency is affected by changing emulsion levels and MW power densities.

The emulsions levels could be evaluated based upon the size of the reactant droplets, such as 1 nm, 5 nm, 10 nm, 50 nm, 100 nm, 200 nm, 300 nm, 400 nm, 500 nm, 1000 nm, or any other desired droplet size. Alternatively, the emulsion levels could be evaluated based upon the time the reactants are subjected to a high-speed mixer (e.g., 20,000 rpm), such as 10 sec., 20 sec., 30 sec., 1 min., 2 min., 3 min., 5 min., 10 min., or any other desired time period.

The MW power densities could be 0.01 W/cc, 0.05 W/cc, 0.10 W/cc, 0.50 W/cc, 1 W/cc, 3 W/cc, 5 W/cc, 10 W/cc, 20 W/cc, 50 W/cc, 100 W/cc, or any other desired power density.

In order to more clearly show the conversion enhancement provided by emulsification and RF or MW energy in combination with the effects of increased pressure, the above-described tests could be performed using a variety of pressure values. The test would involve measuring the time required to achieve 100% conversion using various combinations of emulsification, MW power density, and pressure. Alternatively, the test could involve the measuring of the percent conversion at a given time period, such as 30 or 60 minutes, for various combinations of emulsification, MW power density, and pressure. These tests would show how the reaction efficiency is affected by changing emulsification, MW power density, and pressure. The proposed emulsification and MW power densities are listed above, and the proposed pressures are autogeneous pressure, and 5 psig, 10 psig, 25 psig, 50 psig, and 100 psig above autogeneous pressure, or any other desired pressure.

Each of the above tests relating to emulsion and MW enhancement could also be performed in relation to an esterification process for converting FFAs in order to show the effects of these parameters on esterification. Of course, appropriate process parameters and catalysts (e.g., 2 wt % sulfuric acid) would need to be used.

We claim:

1. A method of converting a triglyceride to an alkyl ester and glycerol using a transesterification process, the method comprising:
   mixing the triglyceride with an alcohol to produce a reactant mixture;
   flowing the reactant mixture over a heterogeneous catalyst with a relative velocity of at least 0.05 m/s to obtain high reactant shear at a reactant-heterogeneous-catalyst interface; and
   producing alkyl ester and glycerol.

2. The method of claim 1, wherein mixing occurs at the same time as flowing.

3. The method of claim 1, wherein the triglyceride are present in at least one of plant oil, animal oil and a combination thereof.

4. The method of claim 3, wherein the triglyceride is present in an oil derived from at least one of soybeans, corn, sunflower, palm, nut, safflower, olives, cotton, linseed, mustard seed, rapeseed, canola, peanuts, coconut, castor beans, tall oil, soapstock, raw or rendered animal fats, brown grease, white grease, yellow grease, lard or tallow from pork, chicken, mutton, beef, horse and combinations thereof, as well as wastes, effluents and residues from the processing of such materials, and combinations thereof.

5. The method of claim 1, wherein the alcohol is a C1-C6 alcohol.

6. The method of claim 5, wherein the alcohol is at least one of methanol and ethanol.

7. The method of claim 1, wherein mixing includes combining the triglyceride and the alcohol in a ratio of at least about 10% alcohol by weight.

8. The method of claim 1, wherein the heterogeneous catalyst comprises an alkaline catalyst or an acid catalyst.

9. The method of claim 8, wherein the heterogeneous catalyst comprises at least one of a hydroxide of Group 1 or 2 metals, a silicate of Group 1 or 2 metals, a carbonate of Group 1 or 2 metals, a strong anion exchange resin in the hydroxide form, an oxide of aluminum and magnesium and mixtures thereof.

10. The method of claim 8, wherein the heterogeneous catalyst is at least one of a zeolite in the acid form, a strong cation exchange resin in the hydrogen form, a Lewis acid, and mixtures thereof.

11. The method of claim 1, further comprising maintaining a pressure at or greater than autogeneous pressure.

12. The method of claim 11, wherein the method takes place at a pressure between about 10 psig and about 100 psig above the autogeneous pressure.

13. The method of claim 1, further comprising applying RF or microwave energy to at least one of the triglyceride, the alcohol, the heterogeneous catalyst, and a combination thereof.

14. The method of claim 13, wherein applying RF or microwave energy includes controlling at least one of a frequency, power density, field strength, and a combination thereof.

15. The method of claim 14, wherein an average power density is maintained between about 0.01 watts/cc and about 100 watts/cc.

16. The method of claim 15, wherein an average power density is maintained between about 0.05 watts/cc and about 10 watts/cc.

17. The method of claim 16, wherein an average power density is maintained between about 0.1 watts/cc and about 3 watts/cc.

18. The method of claim 13, wherein applying RF or microwave energy includes modulating the energy.

19. The method of claim 18, wherein modulating includes at least one of amplitude modulation, frequency modulation, pulse width modulation, and combinations thereof.

20. The method of claim 13, wherein the RF or microwave energy comprises a frequency from about 1 MHz to about 100 GHz.

21. The method of claim 20, wherein the RF or microwave energy comprises a frequency from about 100 MHz to about 10 GHz.

22. The method of claim 21, wherein the RF or microwave energy comprises a frequency from about 400 MHz to about 5 GHz.

* * * * *